(12) United States Patent
Gleave

US008541390B2

(10) Patent No.: US 8,541,390 B2
(45) Date of Patent: *Sep. 24, 2013

(54) TREATMENT OF CANCER BY INHIBITION OF IGFBPS AND CLUSTERIN

(75) Inventor: Martin E. Gleave, Vancouver (CA)

(73) Assignee: The University of British Columbia, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 13/469,402

(22) Filed: May 11, 2012

(65) Prior Publication Data

US 2012/0220646 A1    Aug. 30, 2012

Related U.S. Application Data

(63) Continuation of application No. 13/087,618, filed on Apr. 15, 2011, now Pat. No. 8,252,765, which is a continuation of application No. 11/287,334, filed on Nov. 23, 2005, now Pat. No. 7,973,017, which is a continuation-in-part of application No. 10/346,493, filed on Jan. 17, 2003, now abandoned.

(60) Provisional application No. 60/522,948, filed on Nov. 23, 2004, provisional application No. 60/522,960, filed on Nov. 24, 2004, provisional application No. 60/350,046, filed on Jan. 17, 2002.

(51) Int. Cl.
*A01N 43/04* (2006.01)
*A01N 61/00* (2006.01)
*C07H 21/02* (2006.01)
*C07H 21/04* (2006.01)
*C12Q 1/68* (2006.01)

(52) U.S. Cl.
USPC ............ 514/44; 435/6; 435/91.1; 435/91.31; 435/455; 514/1; 514/2; 536/23.1; 536/24.31; 536/24.5

(58) Field of Classification Search
USPC ................ 435/6, 91.1, 91.31, 455; 514/1, 514/2, 44; 536/23.1, 24.5, 24.3
See application file for complete search history.

(56) References Cited

U.S. PATENT DOCUMENTS

| | | | |
|---|---|---|---|
| 5,417,978 A | 5/1995 | Tari et al. | |
| 5,646,042 A | 7/1997 | Stinchcomb et al. | |
| 5,721,237 A | 2/1998 | Myers et al. | |
| 5,789,389 A | 8/1998 | Tarasewicz et al. | |
| 5,801,154 A | 9/1998 | Baracchini et al. | |
| 5,855,911 A | 1/1999 | Lopez-Berestein et al. | |
| 5,910,583 A | 6/1999 | Marks et al. | |
| 5,929,040 A | 7/1999 | Werther et al. | |
| 5,998,148 A | 12/1999 | Bennett et al. | |
| 6,133,246 A | 10/2000 | McKay et al. | |
| 6,172,216 B1 | 1/2001 | Bennett et al. | |
| 6,284,741 B1 | 9/2001 | Werther et al. | |
| 6,335,194 B1 | 1/2002 | Bennett et al. | |
| 6,365,345 B1 | 4/2002 | Brysch et al. | |
| 6,383,808 B1 | 5/2002 | Monia et al. | |
| 6,451,991 B1 | 9/2002 | Martin et al. | |
| 6,900,187 B2 | 5/2005 | Gleave et al. | |
| 7,196,067 B2 | 3/2007 | Gleave et al. | |
| 7,973,017 B2 * | 7/2011 | Gleave ...................... 514/44 A | |
| 8,252,765 B2 * | 8/2012 | Gleave ...................... 514/44 A | |
| 2002/0086356 A1 | 7/2002 | Tuschi et al. | |
| 2002/0128220 A1 | 9/2002 | Gleave | |
| 2003/0087857 A1 | 5/2003 | Freier | |
| 2003/0105051 A1 | 6/2003 | McSwiggen | |
| 2003/0158130 A1 | 8/2003 | Gleave et al. | |
| 2003/0158143 A1 | 8/2003 | Gleave et al. | |
| 2003/0166591 A1 | 9/2003 | Gleave et al. | |
| 2004/0006106 A1 | 1/2004 | Uesugi et al. | |
| 2004/0053874 A1 | 3/2004 | Monia et al. | |
| 2004/0096882 A1 | 5/2004 | Gleave et al. | |
| 2004/0220131 A1 | 11/2004 | Jackson et al. | |

FOREIGN PATENT DOCUMENTS

| | | |
|---|---|---|
| WO | 9203470 A1 | 3/1992 |
| WO | 9203471 A1 | 3/1992 |
| WO | 0031048 A1 | 6/2000 |
| WO | 0034469 A1 | 6/2000 |
| WO | 0049937 A2 | 8/2000 |
| WO | 0069454 A1 | 11/2000 |
| WO | 0078341 A1 | 12/2000 |

(Continued)

OTHER PUBLICATIONS

Oh et al., Insulin-like Growth Factor (IGF)-independent Action of IGF-binding Protein-3 in Hs578T Human Breast Caner Cells, The Journal of Biological Chemistry, 1993, pp. 14964-14971, vol. 268, No. 20.

Rajaram, Insulin-Like Growth Factor-Binding Proteins in Serum and Other Biological Fluids; Regulation and Functions, Endocrine Reviews, 1997, pp. 801-831, vol. 18, No. 6.

Damon et al., Overexpression of an Inhibitory Insulin-Like Growth Factor Binding Protein (IGFBP), IGFBP-4, Delays Onset of Prostate Tumor Formation, Endocrinology, 1998, pp. 3456-3464, vol. 139, No. 8.

Ziegler et al., Induction of Apoptosis in Small-Cell Lung Cancer Cells by an Antisense Oligodeoxynucleotide Targeting the Bcl-2 Coding, Journal of National Cancer Institute, 1997, vol. 89, No. 14.

Bruchovsky et al., Classification of Dependent and Autonomous Variants of Shionogi Mammary Carcinoma Based on Heterogenous Patterns of Androgen Binding, Cell, 1978, pp. 273-280, vol. 13.

(Continued)

*Primary Examiner* — Jane Zara
(74) *Attorney, Agent, or Firm* — Larson & Anderson, LLC

(57) ABSTRACT

Agents that reduce the amount of IGFBP-2 and/or IGFBP-5 and that are known to be useful in the treatment of cancer result in increased expression of the protein clusterin. Since clusterin can provide protection against apoptosis, this secondary effect detracts from the efficacy of the therapeutic agent. In overcoming this, the present invention provides a combination of therapeutic agents that is useful in the treatment of cancer. The combination includes an agent that reduces the amount of IGFBP-2 and/or IGFBP-5 and that stimulates expression of clusterin as a secondary effect, and an oligonucleotide that is effective to reduce the amount of clusterin in cancer cells. In some embodiments of the invention, the agent that reduces IGFBP-2 and/or IGFBP-5 is a bispecific antisense species. The oligonucleotide may be an antisense oligonucleotide or an RNAi oligonucleotide.

1 Claim, 13 Drawing Sheets

(56) References Cited

FOREIGN PATENT DOCUMENTS

| WO | 0101748 | | 1/2001 |
|---|---|---|---|
| WO | 0105435 | A2 | 1/2001 |
| WO | 0146455 | A2 | 6/2001 |
| WO | 0175164 | A2 | 10/2001 |
| WO | 0222635 | A1 | 3/2002 |
| WO | 0222642 | A1 | 3/2002 |
| WO | 0244321 | A2 | 6/2002 |
| WO | 03030826 | A2 | 4/2003 |
| WO | 03035843 | A2 | 5/2003 |
| WO | 03062421 | A1 | 7/2003 |
| WO | 03072591 | A1 | 9/2003 |
| WO | 2004018675 | A1 | 3/2004 |
| WO | 2004018676 | A2 | 3/2004 |

OTHER PUBLICATIONS

Bruchovsky et al., Effects of Androgen Withdrawal on the Stem Cell Composition of the Shionogi Carcinoma, Cancer Research, 1990, pp. 2275-2282, vol. 50.

Gleave et al., Serum Prostate Specific Antigen Levels in Mice Bearing Human Prostate LNCaP Tumors are Determined by Tumor Volume and Endocrine and Growth Factors, Cancer Research, 1992, pp. 1598-1605, vol. 52.

Gleave et al., Animal Models in Prostate Cancer, Principles and Practice of Genitourinary Oncology, 1997, pp. 367-378, Publisher: Lippincott-Raven.

Gleave et al., Intermittent Androgen Suppression for Prostate Cancer: Rationale and Clinical Experience, European Urology, 1998, pp. 37-41, vol. 34; Suppl. 3.

Gleave et al., Prostate cancer: 9. Treatment of advanced disease, Canadian Medical Association Journal, 1999, pp. 225-232, vol. 160, No. 2.

Gleave et al., Neoadjuvant Androgen Withdrawal Therapy Decreases Local Recurrence Rates Following Tumor Excision in the Shionogi Tumor Model, the Journal of Urology, 1997, pp. 1727-1730, vol. 157, No. 5.

James et al., A Highly Conserved Insulin-like Growth Factor-binding Protein (IGFBP-5) is Expressed during Myoblast Differentiation, The Journal of Biological Chemistry, 1993, pp. 22305-22312. vol. 268, No. 30.

Kiefer et al., Molecular Cloning of a New Human Insulin-like Growth Factor Binding Protein, Biochemical and Biophysical Research Communications, 1991, pp. 219-225, vol. 176, No. 1.

Miyake et al., Overexpression of Insulin-like Growth Factor Binding Protein-5 Helps Accelerate Progression to Androgen-Independence in the Human Prostate LNCaP Tumopr Model through Activation of Phosphatidylinositol 3'-Kinase Pathway, Endocrinology, 2000, pp. 2257-2265, vol. 141, No. 6.

Rennie et al., Gene Expression during the Early Phases of Regression of the Androgen-dependent Shionogi Mouse Mammary Carcinoma, Cancer Research, 1988, pp. 6309-6312, vol. 48.

Gleave et al., Targeting anti-apoptotic genes upregulated by androgen withdrawal using antisense oligonucleotides to enhance androgen- and chemo-sensitivity in prostate cancer, Investigational New Drugs, 2002, pp. 145-158, vol. 20.

Gleave et al., Use of Antisense Oligonucleotides Targeting the Antiapoptotic Gene, Clusterin/Testosterone-Repressed Prostate Message 2, to Enhance Androgen Sensitivity and Chemosensitivity in Prostate Cancer, Urology, 2001, pp. 39-49, vol. 58, XP-002262320.

Gleave et al., Antisense therapy: Current status in prostate cancer and other malignancies, Cancer and Metastasis Reviews, 2002, pp. 79-92, vol. 21.

Jones et al., Molecules in focus: Clusterin, The International Journal of Biochemistry & Cell Biology, 2002, pp. 427-431, vol. 34.

Miyake et al., Antisense TRPM-2 Oligodeoxynucleotides Chemosensitize Human Androgen-Independent PC-3 Prostate Cancer Cells Both in Vitro and in Vivo, Clinical Cancer Research, 2000, pp. 1655-1663, vol. 6, XP-000960694.

Miyake et al., Testosterone-repressed Prostate Message-2 is an Antiapoptotic Gene Involved in Progression to Androgen Independence in Prostate Cancer, Cancer Research, 2000, pp. 170-176. vol. 60, XP-002907064.

Miyake et al., Synergistic chemosensitization and Inhibition of Tumor Growth and Metastasis by the Antisense Oligodeoxynucleotide Targeting Clusterin Gene in a Human Bladder Cancer Model, Clinical Cancer Research, 2001, pp. 4245-4252, vol. 7, Xp-002263075.

Miyake et al., Novel therapeutic strategy for advanced prostate cancer using antisense oligodeoxynucleotides targeting antiapoptotic genes upregulated after androgen withdrawal to delay androgen-independent progression and enhance chemosensitivity, International Journal of Urology, 2001, pp. 337-349, vol. 8, XP-002262321.

Sensibar et al., Prevention of Cell Death Induced by Tumor Necrosis Factor a in LNCaP Cells by Overexpression of Sulfated Glycoprotein-2 (Clusterin), Cancer Research, 1995, pp. 2431-2437, vol. 55, XP-002930082.

Rosenberg et al., Clusterin: Physiologic and Pathophysiologic Considerations, Int. J. Biochem, Cell Biol., 1995, pp. 633-645, vol. 27, No. 7, XP-001002844.

Aoki et al., RNA Intereference may be more potent than antisense RNA in human cancer cell lines, Clinical and Experimental Pharmacology and Physiology, 2003, pp. 96-102.

Benner et al., Combination of Antisense Oligonucleotide and Low-Dose Chemotherapy in Hematological Malignancies, Journal of Pharmacological and Toxicological Methods, 1997, pp. 229-235, Publisher: Elsevier Science Inc.

Boral et al., Clinical evaluation of biologically targeted drugs: obstacles and opportunities, Cancer Chemother. Pharmacol, 1998, pp. S3-S21, Publisher: Springer-Verlag.

Steven Brem, MD, Angiogenesis and Cancer Control: From Concept to Therapeutic Trial, Cancer Control Journal, 1999, vol. 6, No. 5, Publisher: H. Lee Moffitt Cancer Center & Research Institute.

Bruchovsky et al, Control of Tumor Progression by Maintenance of Apoptosis, www.prostatepointer.org, 1996, Publisher: Wiley-Liss, Inc.

Buttyan et al., Induction of the TRPM-2 Gene in Cells Undergoing Programmed Death, Molecular and Cellular Biology, 1989, pp. 3473-3481, vol. 9, No. 8, Publisher: American Society for Microbiology.

Cox et al., Angiogenesis and non-small cell lung cancer, Lung Cancer, 2000, pp. 81-100, Publisher: Elsevier.

Darby et al., Vascular Expression of Clusterin in Experimental Cyclosporine Nephrotoxicity, Exp Nephrol, 1995, pp. 234-239, Publisher: S. Karger AG.

Diemer et al., Expression of Porcine Complement Cytolysis Inhibitor mRNA in Cultured Aortic Smooth Muscle Cells, The Journal of Biological Chemistry, 1992, pp. 5257-5264, vol. 207, No. 8, Publisher: The American Society for Biochemistry and Molecular Biology, Inc.

Genta, New Data Reaffirm Genta's Molecular Target as Critical Factor for Enhancing Anticancer Treatment, www.genta.com, 2001.

Kadomatsu et al., Expression of sulfated glycoprotein 2 is associated with carcinogenesis induced by N-nitroso-N-methylurea in rat prostate, Cancer Res., 1993, pp. 1480-1483, vol. 53, No. 7.

Kirby et al., Bartonella-associated endothelial proliferation depends on inhibition of apoptosis, PNAS, 2002, pp. 4656-4661, vol. 99, No. 7.

Kyprianou et al., bcl-2 over-expression delays radiation-induced apoptosis without affecting the clonogenic survival of human prostate, International Journal of Cancer, 1997, pp. 341-348, vol. 70, No. 3.

Lee et al., In Vitro Models of Prostate Apoptosis: Clusterin as an Antiapoptotic Mediator, The Prostate Supplement, 2000, pp. 21-24, vol. 9, Publisher: Wiley-Liss, Inc.

Millar et al., Localization of mRNAs by in-situ hybridization to the residual body at stages IX-X of the cycle of the rat seminiferous, International Journal of Andrology, 1994, pp. 149-160, Vjol. 17.

Millis et al., Clusterin Regulates Vascular Smooth Muscle Cell Nodule Formation and Migration, Journal of Cellular Physiology, 2001, pp. 210-219, vol. 186, Publisher: Wiley-Liss, Inc.

Milner et al., Selecting effective antisense reagents on combinatorial oligonucleotide arrays, Nature Biotechnology, 1997, pp. 537-541, vol. 15.
Nor et al., Engineering and Characterization of Functional Human Microvessels in Immunodeficient Mice, Laboratory Investigation, 2001, pp. 453-463, vol. 81, No. 4.
Nor et al., Up-Regulation of Bcl-2 in Microvascular Endothelial Cells Enhances Intratumoral Angiogenesis and Accelerates Tumor Growth, Cancer Research, 2001, pp. 2183-2188, vol. 61.
Tran et al., A role for surviving in chemoresistance of endothelial cells mediated by VEGF, PNAS, 2002, pp. 4349-4354, vol. 99, No. 7.
Brummelkamp et al., A system for stable expression of short interfering RNAs in mammalian cells, Science, 2002, pp. 550-553, vol. 296, No. 5567, Publisher: American Association for the Advancement of Science, US.
Calero et al., Apolipoprotein J (Clusterin) and Alzheimer's Disease, Microscopy Research and Technique, 2000, pp. 550-553, vol. 50, No. 4, XP009021345.
Choi-Miura et al., Relationship Between Multifunctional Protein "Clusterin" and Alzheimer Disease, Neurobiology of Aging, 1996, pp. 717-722, vol. 17, No. 5, XP009021345.
Demir et al., Use of RNA Interference (RNAi) to Disrupt C-Kit Gene Expression in Malignant Human Hematopoietic and Neuroepithelial Cells, Blood, 2000, p. 378B, vol. 96, No. 11, Part 2, Publisher: W.B. Saunders Company, Orlando, FL, US XP009004894.
EMBL Accession No. m63376, Genomic organization and expression of the rat TRPM-2 (clusterin) gene, a gene implicated in apoptosis, 1991.
Hohjoh, RNA interference (RNAi) induction with various types of synthetic oligonucleotide duplexes in cultered human cells, FEBS Letters, 2002, pp. 195-199, vol. 521, No. 1-3, Publisher: Elsevier Science Publishers, Amsterdam, NL XP004362164.
Koch-Brandt et al., Clusterin: A Role in Cell Survival in the Face of Apoptosis?, Progress in Molecular and Subcellular Biology, 2004, pp. 130-149, vol. 16, XP009021385.
Paddison et al., Stable suppression of gene expression by RNAi in mammalian cells, Proceedings of the National Academy of Sciences of USA, 2002, pp. 1443-1448, vol. 99, No. 3, Publisher: National Academy of Sciences, XP002958887.
Sharp, RNAi and double-strand RNA, Genes and Development, 1999, pp. 139-141, vol. 13, No. 2, Publisher; Gold Spring Harbor Laboratory Press, New York, US, XP002171268.
Strocchi et al., Neuronal loss up-regulates clusterin mRNA in living neurons and glial cells in the rat brain, NeuroReport, 1999, pp. 1789-1792, vol. 10, No. 8, Publisher: Rapid Communications of Oxford, Oxford, GB, XP009017327.
Sui et al., A DNA vector-based RNAi technology to suppress gene expression in mammalian cells, Proceedings of The National Academy of Sciences of USA, 2002, pp. 5515-5520, vol. 99, No. 8, Publisher: National Academy of Science, Washington, US, XP002964701.
Tuschl et al., Targeted mRNA degradation by double-stranded RNA in vitro, Genes and Development, 1999, pp. 3191-3197, vol. 13, No. 24, Publisher; Cold Spring Harbor Laboratory Press, New York, US, XP002183118.
UEDA, RNAi: A new technology in the post-genomic sequencing era, Journal of Neurogenetics, 2001, pp. 193-204, vol. 15, No. 3/4, Publisher: Elsevier, Amsterdam, NL, XP00114722.:.
Baxevanis et al., Immunobiology of HER-2/neu oncoprotein and its potential in cancer immunotherapy, Cancer Immunol. Immunothr, 2004, pp. 166-175, vol. 53.
Bellmunt et al., Novel approaches with targeted therapies in bladder cancer. Therapy of bladder cancer by blockade of the epidermal, Crit. Rev. Oncol. Hematol., 2003, pp. S85-104, vol. 46 Suppl.
Cianciulli et al., Her-2/neu oncogene amplification and chromosome 17 aneusomy in endometrial carcinoma; correlation with oncoprotein, J. Exp. Clin. Cancer Res., 2003, pp. 265-271, vol. 22.
Di Lorenzo et al., HER-2/neu receptor in prostate cancer development and progression to androgen independence, Tumori, 2004, pp. 163-170, vol. 90.
Half et al., HER-2/neu receptor expression, localization and activation in colorectal cancer cell lines and human tumors, Int. J. Cancer, 2004, pp. 540-548, vol. 108.

Lazebnik et al., Cleavage of poly (ADP-ribose) polymerase by a proteinase with properties like ICE, Nature, 1994, pp. 346-347, vol. 371.
Nathanson et al., HER-2/neu expression and gene amplication in colon cancer, Int. J. Cancer, 2003, pp. 796-802, vol. 105.
Park et al., Clinical significance of HER-2/neu expression in colon cancer, Korean J. Gastroenterol., 2004, pp. 147-152, vol. 44.
Scholl et al., Targeting HER-2 in other tumor types, Annals of Oncology, 2001, pp. S81-87, vol. 12, Suppl 1.
Slamon et al., Use of chemotherapy plus a monoclonal antibody against HER2 for metastatic breast cancer that overexpresses HER2, NEJM, 2001, pp. 783-792, vol. 344, No. 11.
Slomovitz et al., Her-2/neu overexpression and amplification in uterine papillary serous carcinoma, J. Clin. Oncol., 2004, pp. 3126-3132, vol. 22.
Telford et al., Comparative evaluation of several DNA binding dyes in the detection of apoptosis-associated chromatin degradation, Cytometry, 1992, pp. 137-143, vol. 13.
Tiseo et al., Epidermal growth factor receptor inhibitorsL a new prospective in the treatment of lung cancer, Curr. Med. Chem. Anti-Canc. Agents, 2004, pp. 139-148, vol. 4.
Hu et al., Discovery and validation of new molecular targets for ovarian cancer, Curr. Opin. Mol. Ther., 2003, pp. 625-630, vol. 5.
Kunkel et al., Inhibition of Glioma Angiogenesis and Growth in Vivo by Systemic Treatment with a Monoclonal Antibody against Vascular Endothelial Growth Factor Receptor-2' Cancer Research, 2001, pp. 6624-6628, vol. 61.
American Cancer Society, Cancer Facts & Figures 2004, 2004, pp. 1-56, Publisher: American Cancer Society.
Johnson et al., Quality of long-term survival in young children with medulloblastoma, J Neurosurg, 1994, pp. 1004-1010, vol. 80.
Lallana et al., Update on the therapeutic approaches to brain tumors, Exper Rev. Anticancer Ther., 2003, pp. 655-670, vol. 3, No. 5.
Mahaley et al., National survey of patterns of care for brain-tumor patients, J. Neurosurg., 1989, pp. 826-836, vol. 71.
Packer et al., A prospective study of cognitive function in children receiving whole-brain radiotherapy and chemotherapy: 2-year results, J. Neurosurg, 1989, pp. 707-713, vol. 70.
Parkin et al., Estimating the World Cancer Burden: Globocan 2000, Int. J. Cancer, 2001, pp. 153-156, vol. 94.
National Cancer Institute, Trends in SEER Incidence and US Mortality Using the Joinpoint Regression Program, 1975-2000 With Up to Three Joinpoints by Race and Sex, SEER Cancer Statistics Review 1975-2000, 2000, Publisher: National Cancer Institute.
Strother et al., Tumors of the Central Nervous System, Principles and Practice of Pediatric Oncology, 4th Edition, 2002, pp. 751-824, Publisher : Lippincott Williams & Wilkins.
Surawicz et al., Brain tumor survival; Results from the National Cancer Data Base, Journal of Neuro-Oncology, 1998, pp. 151-160, vol. 40.
Andress et al., Human Osteoblast-derived Insulin-like Growth Factor (IGF) Binding Protein-5 Stimulates Osteoblast—Mitogenesis and Potentiates IGF Action, Journal of Biological Chemistry, 1992, pp. 22467-22472, vol. 267, No. 31.
Crooke et al., Basic Principles of Antisense Therapeutics, Antisense Research and Application, 2004, pp. 1-50, Publisher: Springer.
Jen et al., Suppression of Gene Expression by Targeted Disruption of Messenger RNA: Available Options and Current Strategies, Stem Cells 2000, 2000, pp. 307-319, vol. 18.
Angelloz-Nichoud et al., Autocrine Regulation of Cell Proliferation by the Insulin-Like Growth Factor (IGF) and IGF Binding Protein-3 Protease system in a Human Prostate Carcinoma Cell Line (PC-3), Endocrinology, 1995, pp. 5485-5492, vol. 136, No. 12.
Bouden et al., Secretion of Insulin-Like Growth Factors and Their Binding Proteins by Human Normal and Hyperplastic Prostatic Cells in Primary Culture, Journal of Clinical Endocrinology and Metabolism, 1996, pp. 612-617, vol. 81, No. 2.
Cucco et al., In Vitro and in Vivo Reversal of Multidrug Resistance in a Human Leukemia-resistant Cell Line by mdr1 Antisense Oligodeoxynucleotides, Cancer Research, 1996, pp. 4332-4337, vol. 56.

Elgin et al., An insulin-like growth factor (IGF) binding protein enhances the biologic response to IGF-I, Cell Biology, 1987, pp. 3254-3258, vol. 84, Publisher: Proc. Natl. Acad. Sci.

Figueroa et al., Differential Expression of Insulin-Like Growth Factor Binding Proteins in High Versus Low Gleason Score Prostate Cancer, The Journal of Urology, 1998, pp. 1379-1383, vol. 159, No. 4.

Huynh et al., Estradiol and Antiestrogens Regulate a Growth Inhibitory Insulin-like Growth Factor Binding Protein 3 Autocrine Loop in Human Breast Cancer Cells, The Journal of Biological Chemistry, 1996, pp. 1016-1021, vol. 271, No. 2.

Jansen et al., bcl-2 antisense therapy chemosensitizes human melanoma in SCID mice, Nature Medicine, 1998, vol. 4, No. 2.

Monia et al., Antitumor Activity of a Phosphorothioate Antisense Oligodeoxynucleotide Targeted against C-raf Kinase, Nature Medicine, 1996, pp. 668-675, vol. 2, No. 6.

Nickerson et al., Castration-induced apoptosis in the rat ventral prostate is associated with increased expression of genes encoding insulin-like growth factor binding proteins 2,3,4 and 5, Endocrinology, 1998, pp. 807-810, vol. 139, No. 2.

Oh et al., Management of Hormone Refractory Prostate Cancer: Current Standards and Future Prospects, The Journal of Urology, 1998, pp. 1220-1229, vol. 160, No. 4.

Opalinska et al., Nucleic-Acid Therapeutics: Basic Principles and Recent Applications, Nature Reviews, 2002, pp. 503-514, vol. 1.

Holen et al., Positional effects of short interfering RNAs targeting the human coagulation trigger Tissue Factor, Nucleic Acids Research, 2002, pp. 1757-1766, vol. 30, No. 8.

Binkert et al., Structure of the Human Insulin-Like Growth Factor Binding Protein-2 Gene, Molecular Endocrinology, 1992, pp. 826-836, vol. 6, No. 5.

Bubendorf et al., Hormone Therapy Failure in Human Prostate Cancer: Analysis by Complementary DNA and Tissue Microarrays, Journal of the National Cancer Institute, 1999, pp. 1758-1764, Bol. 91, No. 20.

Corkins et al., Growth Stimulation by Transfection of Intestinal Epithelial Cells with an Antisense Insulin-Like Growth Factor Binding Protein-2 Construct, Biochemical and Biophysical Research Communications, 1995, pp. 707-713, vol. 211, No. 3.

Forsyth et al., Growth Inhibition of a Human Colon Cancer Cell Line by Antisense Oligonucleotide to IGFBP-2, 1995, p. A726, vol. 108, No. 4.

Gleave et al., Antisense Targets to Enhance Hormone and Cytotoxic Therapies in Advanced Prostate Cancer, Current Drug Targets, 2003, pp. 209-221, vol. 4, No. 3.

Miyake et al., Castration-Induced Up-Regulation of Insulin-Like Growth Factor Binding Protein-5 Potentiates Insulin-Like Growth Factor-I Activity and Accelerates Progression to Androgen Independence in Prostate Cancer Models, Cancer Research, 2000, pp. 3058-3064, vol. 60.

Steller et al., Insulin-like growth factor II mediates epidermal growth factor-induced mitogenesis in cervical cancer cells, Proc. Natl. Acad. Sci.—Cell Biology, 1995, pp. 11970-11974, vol. 92.

Wang et al., Correlation of Glioma Cell Regression with Inhibition of Insulin-Like Growth Factor I and Insulin-Like Growth Factor-Binding Protein-2 Expression, Neuroendrocrinology, 1997, pp. 203-211. vol. 66.

Shimasaki et al., Identificaion of Five Different Insulin-like Growth Factor Binding Proteins (IGFBP's) from Adult Rat Serum and Molecular Cloning of a Novel IGFBP-5 in Rat and Human, Journal of Biological Chemistry, 1991, pp. 10646-10653, vol. 266, No. 16.

Zangemeister-Wittke et al., A Novel Bispecific Antisense Oligonucleotde Inhibiting both bcl-2 and bcl-xL Expression Efficiently Induces Apoptosis in Tumor Cells, Clinical Cancer Research: An Official Journal of the American Association for Cancer Research, 2000, pp. 2547-2555, vol. 6, No. 6.

Tamm et al., Antisense therapy in oncology: new hope for an old idea?, The Lancet, pp. 489-497, vol. 358, No. 9280.

Agrawal, Antisense oligonucleotides: towards clinical trials, TIBTECH, 1996, pp. 376-387, vol. 14.

Gewirtz et al., Facilitating oligonucleotide delivery: Helping antisense deliver on its promise, Proc. Natl. Acad. Sci., 1996, pp. 3161-3163, vol. 93.

Gregory, Androgen Receptor Up-Regulates Insulin-Like Growth Factor Binding Protein-5 (IGFBP-5) Expression in a Human Prostate Cancer Xenograft, Endocrinology, 1999, pp. 2372-2381, vol. 140, No. 5.

Huynh et al., A Role for Insulin-like Growth Factor Binding Protein 5 in the Antiproliferative Action of the Antiestrogen ICI 182780, Cell Growth and Differentiation, 1996, pp. 1501-1506, vol. 7.

Nickerson et al., Castration-Induced Apoptosis of Androgen-dependent Shionogi Carcinoma is Associated with Increased Expression of Genes, Cancer Research, 1999, pp. 3392-3395, vol. 59.

Reuters, Isis Antisense Drug Fails in Trial, New Release, Mar. 17, 2003.

Levitt Jr. et al., Bispecific antisense oligonucleotide targeitng both IGFBP-2 and IGFBP-5 inhibits growth of U87 glioma cells, Growth Hormone & IGF Research, 2004, p. 118, vol. 14, No. 2.

Zumkeller, IGFs and IGF-binding proteins as diagnostic markers and biological modulators in brain tumors, Expert Rev Mol Diagn., 2002, pp. 473-477, vol. 2, No. 5.

Wilson et al., Clusterin is a secreted mammalian chaperone, TIBS, 2000, pp. 95-97, vol. 25.

Wong et al., Molecular characterization of human TRPM-2/clusterin, a gene associated with sperm maturation, apoptosis and neurodegeneration, Eur. J. Biochem, 1994, pp. 917-925, vol. 91, XP-001146404.

Green et al., Antisense Oligonucleotides: An Evolving Technology for the Modulation of Gene Expression in Human Disease, J Am Coll Surg,, 2000, pp. 93-105, vol. 191, No. 1.

Zellweger et al., Antitumor Activity of Antisense Clusterin Oligonucleotides is Improved in Vitro and in Vvo by Incorporation of 2'O'(2-Methoxy)Ethyl Chemistry, The Journal of Pharmacology and Experimental Therapeutics, 2001, pp. 934-940, vol. 298, No. 3, XP-002262318.

Zellweger et al., Chemosensitization of Human Renal Cell Cancer Using Antisense Oligonucleotides Targeting the Antiapoptotic Gene Clusterin, Neoplasia, 2001, pp. 360-367, XP-009004604.

Chako et al., Double-stranded ribonucleic acid decreases C6 rat glioma cell numbers: Effects on insulin-like growth factor I gene expression and action, Endocrinology, 2000, pp. 3546-3555, vol. 141, No. 10.

Pavelic et al., Insulin-like growth factor family and combined antisense approach in therapy of lung carcinoma, Molecular Medicine, 2002, pp. 149-157, vol. 8, No. 3.

Agrawal et al., Antisense therapeutics: is it as simple as complementary base recognition?, Molecular Med. Today, 2000, pp. 72-81, vol. 6.

Branch, A good antisense molecule is hard to find, Trends in Biochem. Sci, 1998, pp. 45-50, vol. 23.

Crooke, Progress in Antisense Technology, Annu. Rev. Med., 2004, pp. 61-95, vol. 55.

Peracchi., Prospects for antiviral ribozymes and deoxyribozymes, Rev. Med. Virol., 2004, pp. 47-64, vol. 14.

Chirila et al., The use of synthetic polymers for delivery of therapeutic antisense oligodeoxynucleotides, Biomaterials, 2002, pp. 321-342, vol. 23.

Davies et al., Mutations of the BRAF gene in human cancer, Nature, 2002, pp. 949-954, vol. 417.

Gewirtz, A Critical Evaluation of the Mechanisms of Action Proposed for the Antitumor Effects of the Anthracycline Antibiotics Adriamycin and Daunorubicin, Biochemical Pharmacology, 1999, pp. 727-741, vol. 57.

Harborth et al., Identification of essential genes in cultured mammalian cells using small interfering RNAs, Journal of Cell Science, 2001, pp. 4557-4565, vol. 114.

Leskov et al., Synthesis and Functional Analyses of Nuclear Clusterin, a Cell Death Protein, The Journal of Biological Chemistry, 2003, pp. 11590-11600, vol. 278, No. 13.

McGill et al., Bcl2 Regulation by the Melanocyte Master Regulator Mitf Modulates Lineage Survival and Melanoma Cell Viability, Cell, 2002, pp. 707-718, vol. 109.

Muller et al., Cellular pharmacokinetics of doxorubicin in patients with chronic lymphocytic leukemia: comparison of bolus administration and continuous infusion, Cancer Chemotherapy and Pharmacology, 1993, pp. 379-384, vol. 32.

Rohlff et al., Prostate Cancer Cell Growth Inhibition by Tamoxifen is Associated With Inhibition of Protein Kinase C and Induction of p21, The Prostate, 1998, pp. 51-59, vol. 37.

Carthew et al., Gene silencing by double-stranded RNA, Current Opinion in Cell Biology, 2001, pp. 244-248, vol. 13.

Demattos et al., Clusterin promotes amyloid plaque formation and is critical for neuritic toxicity in a mouse model of Alzheimer's disease, PNAS, 2002, pp. 10843-10848, vol. 99, No. 16.

Elbashir et al., Duplexes of 21—nucleotide RNAs mediate RNA interference in cultured mammalian cells, Nature, 2001, pp. 494-498, vol. 411.

Fire et al., Potent and specific genetic interference by double-stranded RNA in *Caenorhabditis elegans*, Nature, 1998, pp. 806-811, vol. 391.

Trougakos et al., Silencing Expression of the Clusterin/Apolipoprotein J Gene in Human Cancer Cells Using Small Interfering RNA Induces, Cancer Research, 2004, pp. 1834-1842, vol. 64.

Vickers et al., Efficient Reduction of Target RNAs by Small Interfering RNA and RNase H-dependent Antisense Agents, The Journal of Biological Chemistry, 2003, pp. 7103-7118, vol. 278, No. 9.

Wright et al., A ribonucleotide reductase inhibitor, MDL 101,731, induces apoptosis and elevates TRPM-2 mRNA levels in human prostate, Experimental Cell Research, 1996, pp. 54-60, vol. 222, No. 1.

Yang et al., Nuclear clusterin/XIP8, an x-ray-induced Ku70-binding protein that signals cell death, PNAS, 2000, pp. 5907-5912, vol. 97, No. 11.

Zwain et al., Clusterin Protects Granulosa Cells from Apoptotic Cell Death during Follicular Atresia, Experimental Cell Research, 2000, pp. 101-110, vol. 257, Publisher: Academic Press.

Agami, RNAi and related mechanisms and their potential use for therapy, Current Opinion in Chemical Biology, 2002, pp. 829-834, vol. 6, Publisher: Current Biology Ltd, London, GB XP00295888.

* cited by examiner

SEQUENCE LISTING

<160> NUMBER OF SEQ ID NOS: 139

<210> SEQ ID NO 1
<211> LENGTH: 2859
<212> TYPE: DNA
<213> ORGANISM: Homo sapiens

<400> SEQUENCE: 1

```
ctttccgcgg cattctttgg gcgtgagtca tgcaggtttg cagccagccc caaaggggt      60
gtgtgcgcga gcagagcgct ataaatacgg cgcctcccag tgcccacaac gcggcgtcgc    120
caggaggagc gcgcgggcac agggtgccgc tgaccgaggc gtgcaaagac tccagaattg    180
gaggcatgat gaagactctg ctgctgtttg tggggctgct gctgacctgg gagagtgggc    240
aggtcctggg ggaccagacg gtctcagaca atgagctcca ggaaatgtcc aatcagggaa    300
gtaagtacgt caataaggaa attcaaaatg ctgtcaacgg ggtgaaacag ataaagactc    360
tcatagaaaa aacaaacgaa gagcgcaaga cactgctcag caacctagaa gaagccaaga    420
agaagaaaga ggatgcccta aatgagacca gggaatcaga gacaaagctg aaggagctcc    480
caggagtgtg caatgagacc atgatggccc tctgggaaga gtgtaagccc tgcctgaaac    540
agacctgcat gaagttctac gcacgcgtct gcagaagtgg ctcaggcctg gttggccgcc    600
agcttgagga gttcctgaac cagagctcgc ccttctactt ctggatgaat ggtgaccgca    660
tcgactccct gctggagaac gaccggcagc agacgcacat gctggatgtc atgcaggacc    720
acttcagccg cgcgtccagc atcatagacg agctcttcca ggacaggttc ttcacccggg    780
agccccagga tacctaccac tacctgccct tcagcctgcc ccaccggagg cctcacttct    840
tctttcccaa gtcccgcatc gtccgcagct tgatgccctt ctctccgtac gagccctga     900
acttccacgc catgttccag cccttccttg agatgataca cgaggctcag caggccatgg    960
acatccactt ccatagcccg gccttccagc acccgccaac agaattcata cgagaaggcg   1020
acgatgaccg gactgtgtgc cgggagatcc gccacaactc cacgggctgc ctgcggatga   1080
aggaccagtg tgacaagtgc cgggagatct tgtctgtgga ctgttccacc aacaacccct   1140
cccaggctaa gctgcggcgg gagctcgacg aatccctcca ggtcgctgag aggttgacca   1200
ggaaatacaa cgagctgcta aagtcctacc agtggaagat gctcaacacc tcctccttgc   1260
tggagcagct gaacgagcag tttaactggg tgtcccggct ggcaaacctc acgcaaggcg   1320
aagaccagta ctatctgcgg gtcaccacgg tggcttccca cacttctgac tcggacgttc   1380
cttccggtgt cactgaggtg gtcgtgaagc tctttgactc tgatcccatc actgtgacgg   1440
tccctgtaga agtctccagg aagaaccccta aatttatgga gaccgtggcg gagaaagcgc   1500
tgcaggaata ccgcaaaaag caccgggagg agtgagatgt ggatgttgct tttgcaccta   1560
cgggggcatc tgagtccagc tcccccaag atgagctgca gccccccaga gagagctctg    1620
cacgtcacca agtaaccagg ccccagcctc caggccccca actccgccca gcctctcccc   1680
gctctggatc ctgcactcta acactcgact ctgctgctca tgggaagaac agaattgctc   1740
```

```
ctgcatgcaa ctaattcaat aaaactgtct tgtgagctga tcgcttggag ggtcctcttt    1800
ttatgttgag ttgctgcttc ccggcatgcc ttcattttgc tatgggggc aggcaggggg     1860 gatggaaaat aagtagaaac aaaaaagcag tggctaagat ggtataggga ctgtcatacc    1920
agtgaagaat aaagggtga agaataaaag ggatatgatg acaaggttga tccacttcaa     1980
gaattgcttg ctttcaggaa gagagatgtg tttcaacaag ccaactaaaa tatattgctg    2040
caaatggaag cttttctgtt ctattataaa actgtcgatg tattctgacc aaggtgcgac    2100
aatctcctaa aggaatacac tgaaagttaa ggagaagaat cagtaagtgt aaggtgtact    2160
tggtattata atgcataatt gatgttttcg ttatgaaaac atttggtgcc cagaagtcca    2220
aattatcagt tttatttgta agagctattg cttttgcagc ggttttattt gtaaaagctg    2280
ttgatttcga gttgtaagag ctcagcatcc caggggcatc ttcttgactg tggcatttcc    2340
tgtccaccgc cggtttatat gatcttcata ccttcccctg gaccacaggc gtttctcggc    2400
ttttagtctg aaccatagct gggctgcagt accctacgct gccagcaggt ggccatgact    2460
acccgtggta ccaatctcag tcttaaagct caggcttttc gttcattaac attctctgat    2520
agaattctgg tcatcagatg tactgcaatg gaacaaaact catctggctg catcccaggt    2580
gtgtagcaaa gtccacatgt aaatttatag cttagaatat tcttaagtca ctgtcccttg    2640
tctctctttg aagttataaa caacaaactt aaagcttagc ttatgtccaa ggtaagtatt    2700
ttagcatggc tgtcaaggaa attcagagta aagtcagtgt gattcactta atgatataca    2760
ttaattagaa ttatggggtc agaggtattt gcttaagtga tcataattgt aaagtatatg    2820
tcacattgtc acattaatgt caaaaaaaaa aaaaaaaa                            2859
```

<210> SEQ ID NO 2
<211> LENGTH: 21
<212> TYPE: DNA
<213> ORGANISM: Homo sapiens

<400> SEQUENCE: 2
gcacagcagg agaatcttca t                                              21

<210> SEQ ID NO 3
<211> LENGTH: 21
<212> TYPE: DNA
<213> ORGANISM: Homo sapiens

<400> SEQUENCE: 3
tggagtcttt gcacgcctcg g                                              21

<210> SEQ ID NO 4
<211> LENGTH: 21
<212> TYPE: DNA
<213> ORGANISM: Homo sapiens

<400> SEQUENCE: 4
cagcagcaga gtcttcatca t                                              21

<210> SEQ ID NO 5
<211> LENGTH: 21
<212> TYPE: DNA
<213> ORGANISM: Homo sapiens

<400> SEQUENCE: 5
attgtctgag accgtctggt c                                              21

-continued

```
<210> SEQ ID NO 6
<211> LENGTH: 21
<212> TYPE: DNA
<213> ORGANISM: Homo sapiens

<400> SEQUENCE: 6
ccttcagctt tgtctctgat t                                           21

<210> SEQ ID NO 7
<211> LENGTH: 21
<212> TYPE: DNA
<213> ORGANISM: Homo sapiens

<400> SEQUENCE: 7
agcagggagt cgatgcggtc a                                           21

<210> SEQ ID NO 8
<211> LENGTH: 21
<212> TYPE: DNA
<213> ORGANISM: Homo sapiens

<400> SEQUENCE: 8
atcaagctgc ggacgatgcg g                                           21

<210> SEQ ID NO 9
<211> LENGTH: 21
<212> TYPE: DNA
<213> ORGANISM: Homo sapiens

<400> SEQUENCE: 9
gcaggcagcc cgtggagttg t                                           21

<210> SEQ ID NO 10
<211> LENGTH: 21
<212> TYPE: DNA
<213> ORGANISM: Homo sapiens

<400> SEQUENCE: 10
ttcagctgct ccagcaagga g                                           21

<210> SEQ ID NO 11
<211> LENGTH: 21
<212> TYPE: DNA
<213> ORGANISM: Homo sapiens

<400> SEQUENCE: 11
aatttagggt tcttcctgga g                                           21

<210> SEQ ID NO 12
<211> LENGTH: 21
<212> TYPE: DNA
<213> ORGANISM: Homo sapiens

<400> SEQUENCE: 12
gctgggcgga gttgggggcc t                                           21

<210> SEQ ID NO 13
<211> LENGTH: 17
<212> TYPE: DNA
<213> ORGANISM: Homo sapiens

<400> SEQUENCE: 13
ggtgtagacg ccgcacg                                                17
```

```
<210> SEQ ID NO 14
<211> LENGTH: 16
<212> TYPE: DNA
<213> ORGANISM: Homo sapiens

<400> SEQUENCE: 14
gcagcgcagc ccctgg                                                       16

<210> SEQ ID NO 15
<211> LENGTH: 22
<212> TYPE: DNA
<213> ORGANISM: Homo sapiens

<400> SEQUENCE: 15
gcagcagccg cagcccggct cc                                                22

<210> SEQ ID NO 16
<211> LENGTH: 18
<212> TYPE: DNA
<213> ORGANISM: Homo sapiens

<400> SEQUENCE: 16
agccgcagcc cggctcct                                                     18

<210> SEQ ID NO 17
<211> LENGTH: 20
<212> TYPE: DNA
<213> ORGANISM: Homo sapiens

<400> SEQUENCE: 17
cagcagccgc agcccggctc                                                   20

<210> SEQ ID NO 18
<211> LENGTH: 20
<212> TYPE: DNA
<213> ORGANISM: Homo sapiens

<400> SEQUENCE: 18
gcagcagccg cagcccggct                                                   20

<210> SEQ ID NO 19
<211> LENGTH: 20
<212> TYPE: DNA
<213> ORGANISM: Homo sapiens

<400> SEQUENCE: 19
agcagccgca gcccggctcc                                                   20

<210> SEQ ID NO 20
<211> LENGTH: 21
<212> TYPE: DNA
<213> ORGANISM: artificial sequence
<220> FEATURE:
<223> OTHER INFORMATION: mismatch primer

<400> SEQUENCE: 20
cagcagcaga gtatttatca t                                                 21

<210> SEQ ID NO 21
<211> LENGTH: 21
<212> TYPE: DNA
<213> ORGANISM: Homo sapiens

<400> SEQUENCE: 21
guagaagggc gagcucuggu t                                                 21
```

```
<210> SEQ ID NO 22
<211> LENGTH: 21
<212> TYPE: DNA
<213> ORGANISM: Homo sapiens

<400> SEQUENCE: 22
gaugcucaac accuccucct t                                              21

<210> SEQ ID NO 23
<211> LENGTH: 21
<212> TYPE: DNA
<213> ORGANISM: Homo sapiens

<400> SEQUENCE: 23
ggaggaggug uugagcauct t                                              21

<210> SEQ ID NO 24
<211> LENGTH: 21
<212> TYPE: DNA
<213> ORGANISM: Homo sapiens

<400> SEQUENCE: 24
cuaauucaau aaaacuguct t                                              21

<210> SEQ ID NO 25
<211> LENGTH: 21
<212> TYPE: DNA
<213> ORGANISM: Homo sapiens

<400> SEQUENCE: 25
gacaguuuua uugaauuagt t                                              21

<210> SEQ ID NO 26
<211> LENGTH: 19
<212> TYPE: DNA
<213> ORGANISM: Homo sapiens

<400> SEQUENCE: 26
uaauucaaca aaacugutt                                                 19

<210> SEQ ID NO 27
<211> LENGTH: 19
<212> TYPE: DNA
<213> ORGANISM: Homo sapiens

<400> SEQUENCE: 27
acaguuuugu ugaauuatt                                                 19

<210> SEQ ID NO 28
<211> LENGTH: 21
<212> TYPE: DNA
<213> ORGANISM: Homo sapiens

<400> SEQUENCE: 28
augaugaaga cucugcugct t                                              21

<210> SEQ ID NO 29
<211> LENGTH: 21
<212> TYPE: DNA
<213> ORGANISM: Homo sapiens

<400> SEQUENCE: 29
gcagcagagu cuucaucaut t                                              21
```

```
<210> SEQ ID NO 30
<211> LENGTH: 22
<212> TYPE: DNA
<213> ORGANISM: Homo sapiens

<400> SEQUENCE: 30
ugaaugaagg gacuaaccug tt                                              22

<210> SEQ ID NO 31
<211> LENGTH: 22
<212> TYPE: DNA
<213> ORGANISM: Homo sapiens

<400> SEQUENCE: 31
cagguuaguc ccuucauuca tt                                              22

<210> SEQ ID NO 32
<211> LENGTH: 22
<212> TYPE: DNA
<213> ORGANISM: Homo sapiens

<400> SEQUENCE: 32
cagaaauaga caaagugggg tt                                              22

<210> SEQ ID NO 33
<211> LENGTH: 22
<212> TYPE: DNA
<213> ORGANISM: Homo sapiens

<400> SEQUENCE: 33
ccccacuuug ucuauuucug tt                                              22

<210> SEQ ID NO 34
<211> LENGTH: 22
<212> TYPE: DNA
<213> ORGANISM: Homo sapiens

<400> SEQUENCE: 34
acagagacua agggaccaga tt                                              22

<210> SEQ ID NO 35
<211> LENGTH: 22
<212> TYPE: DNA
<213> ORGANISM: Homo sapiens

<400> SEQUENCE: 35
acagagacua agggaccaga tt                                              22

<210> SEQ ID NO 36
<211> LENGTH: 21
<212> TYPE: DNA
<213> ORGANISM: Homo sapiens

<400> SEQUENCE: 36
ccagagcucg cccuucuact t                                               21

<210> SEQ ID NO 37
<211> LENGTH: 21
<212> TYPE: DNA
<213> ORGANISM: Homo sapiens

<400> SEQUENCE: 37
guagaagggc gagcucuggt t                                               21
```

```
<210> SEQ ID NO 38
<211> LENGTH: 21
<212> TYPE: DNA
<213> ORGANISM: Homo sapiens

<400> SEQUENCE: 38
gucccgcauc guccgcagct t                                              21

<210> SEQ ID NO 39
<211> LENGTH: 21
<212> TYPE: DNA
<213> ORGANISM: Homo sapiens

<400> SEQUENCE: 39
gcugcggacg augcgggact t                                              21

<210> SEQ ID NO 40
<211> LENGTH: 21
<212> TYPE: DNA
<213> ORGANISM: Homo sapiens

<400> SEQUENCE: 40
cuaauucaau aaaacuguct t                                              21

<210> SEQ ID NO 41
<211> LENGTH: 21
<212> TYPE: DNA
<213> ORGANISM: Homo sapiens

<400> SEQUENCE: 41
gacaguuuua uugaauuagt t                                              21

<210> SEQ ID NO 42
<211> LENGTH: 19
<212> TYPE: RNA
<213> ORGANISM: Homo sapiens

<400> SEQUENCE: 42
augaugaaga cucugcugc                                                 19

<210> SEQ ID NO 43
<211> LENGTH: 19
<212> TYPE: RNA
<213> ORGANISM: Homo sapiens

<400> SEQUENCE: 43
gcagcagagu cuucaucau                                                 19

<210> SEQ ID NO 44
<211> LENGTH: 21
<212> TYPE: DNA
<213> ORGANISM: Homo sapiens

<400> SEQUENCE: 44
ccagagcucg cccuucuact t                                              21

<210> SEQ ID NO 45
<211> LENGTH: 17
<212> TYPE: DNA
<213> ORGANISM: Homo sapiens

<400> SEQUENCE: 45
ggtgtagacg ccgcacg                                                   17
```

<210> SEQ ID NO 46
<211> LENGTH: 16
<212> TYPE: DNA
<213> ORGANISM: Homo sapiens

<400> SEQUENCE: 46
gcagcgcagc ccctgg                                                   16

<210> SEQ ID NO 47
<211> LENGTH: 22
<212> TYPE: DNA
<213> ORGANISM: Homo sapiens

<400> SEQUENCE: 47
gcagcagccg cagcccggct cc                                            22

<210> SEQ ID NO 48
<211> LENGTH: 18
<212> TYPE: DNA
<213> ORGANISM: Homo sapiens

<400> SEQUENCE: 48
agccgcagcc cggctcct                                                 18

<210> SEQ ID NO 49
<211> LENGTH: 20
<212> TYPE: DNA
<213> ORGANISM: Homo sapiens

<400> SEQUENCE: 49
cagcagccgc agcccggctc                                               20

<210> SEQ ID NO 50
<211> LENGTH: 20
<212> TYPE: DNA
<213> ORGANISM: Homo sapiens

<400> SEQUENCE: 50
gcagcagccg cagcccggct                                               20

<210> SEQ ID NO 51
<211> LENGTH: 20
<212> TYPE: DNA
<213> ORGANISM: Homo sapiens

<400> SEQUENCE: 51
agcagccgca gcccggctcc                                               20

<210> SEQ ID NO 52
<211> LENGTH: 1439
<212> TYPE: DNA
<213> ORGANISM: Homo sapiens

<400> SEQUENCE: 52
tgcggcggcg agggaggagg aagaagcgga ggaggcggct cccgcgctcg cagggccgtg    60
ccacctgccc gcccgcccgc tcgctcgctc gcccgccgcg ccgcgctgcc gaccgccagc   120
atgctgccga gagtgggctg ccccgcgctg ccgctgccgc cgccgccgct gctgcgcctg   180
ctgccgctgc tgctgctgct actgggcgcg agtggcggcg gcggcggggc gcgcgcggag   240
gtgctgttcc gctgcccgcc ctgcacaccc gagcgcctgg ccgcctgcgg gccccgcgcc   300
gttgcgccgc ccgccgcggt ggccgcagtg gccggaggcg cccgcatgcc atgcgcggag   360

```
ctcgtccggg agccgggctg cggctgctgc tcggtgtgcg cccggctgga gggcgaggcg        420
tgcggcgtct acaccccgcg ctgcggccag gggctgcgct gctatcccca cccgggctcc        480
gagctgcccc tgcaggcgct ggtcatgggc gagggcactt gtgagaagcg ccggacgcc         540 gagtatggcg ccagcccgga gcaggttgca gacaatggcg atgaccactc agaaggaggc        600
ctggtggaga accacgtgga cagcaccatg aacatgttgg gcggggagg cagtgctggc         660 cggaagcccc tcaagtcggg tatgaaggag ctggccgtgt ccgggagaa ggtcactgag         720 cagcaccggc agatgggcaa gggtggcaag catcaccttg gcctggagga gcccaagaag        780
ctgcgaccac cccctgccag gactccctgc aacaggaac tggaccaggt cctggagcgg         840
atctccacca tgcgccttcc ggatgagcgg ggccctctgg agcacctcta ctccctgcac        900
atccccaact gtgacaagca tggcctgtac aacctcaaac agtgcaagat gtctctgaac        960
gggcagcgtg gggagtgctg gtgtgtgaac cccaacaccg gaagctgat ccagggagcc        1020 cccaccatcc gggggggaccc cgagtgtcat ctcttctaca atgagcagca ggaggctcgc       1080
ggggtgcaca cccagcggat gcagtagacc gcagccagcc ggtgcctggc gcccctgccc       1140
cccgcccctc tccaaacacc ggcagaaaac ggagagtgct gggtggtgg gtgctggagg       1200 attttccagt tctgacacac gtatttatat ttggaaagag accagcaccg agctcggcac       1260 ctcccccggcc tctctcttcc cagctgcaga tgccacacct gctccttctt gctttccccg       1320
ggggaggaag ggggttgtgg tcggggagct ggggtacagg tttggggagg gggaagagaa       1380 attttattt ttgaaccct gtgtcccttt tgcataagat taaaggaagg aaaagtaaa         1439

<210> SEQ ID NO 53
<211> LENGTH: 6316
<212> TYPE: DNA
<213> ORGANISM: Homo sapiens

<400> SEQUENCE: 53
tagtctcttt ggaaacttct gcaggggaaa agagctagga aagagctgca aagcagtgtg         60 ggcttttttcc cttttttgct ccttttcatt accccctcctc cgtttcacc cttctccgga      120 cttcgcgtag aacctgcgaa tttcgaagag gaggtggcaa agtgggagaa aagaggtgtt      180
agggtttggg gttttttttgt ttttgttttt gtttttttaat ttcttgatt caacatttc       240 tcccacccctc tcggctgcag ccaacgcctc ttacctgttc tgcggcgccg cgcaccgctg      300
gcagctgagg gttagaaagc ggggtgtatt ttagatttta agcaaaaatt ttaaagataa       360 atccatttt ctctcccacc cccaacgcca tctccactgc atccgatctc attatttcgg       420
tggttgcttg ggggtgaaca atttttgtggc tttttttccc ctataattct gacccgctca      480
ggcttgaggg tttctccggc ctccgctcac tgcgtgcacc tggcgctgcc ctgcttcccc       540
caacctgttg caaggcttta attcttgcaa ctgggacctg ctcgcaggca ccccagccct       600
ccacctctct ctacatttt gcaagtgtct gggggagggc acctgctcta cctgccagaa        660
atttaaaaac aaaacaaaa acaaaaaat ctccggggc cctcttggcc ccttttatccc        720 tgcactctcg ctctcctgcc ccaccccgag gtaaagggg cgactaagag aagatggtgt       780
tgctcaccgc ggtcctcctg ctgctggccg cctatgcggg gccggccag agcctgggct       840 ccttcgtgca ctgcgagccc tgcgacgaga aagccctctc catgtgcccc ccagccccc        900 tgggctgcga gctggtcaag gagccgggct gcggctgctg catgacctgc gccctggccg      960
aggggcagtc gtgcggcgtc tacaccgagc gctgcgccca gggctgcgc tgcctccccc       1020 ggcaggacga ggagaagccg ctgcacgccc tgctgcacgg ccgcggggtt tgcctcaacg       1080
```

```
aaaagagcta ccgcgagcaa gtcaagatcg agagagactc ccgtgagcac gaggagccca   1140
ccacctctga gatggccgag gagacctact cccccaagat cttccggccc aaacacaccc   1200
gcatctccga gctgaaggct gaagcagtga agaaggaccg cagaaagaag ctgacccagt   1260
ccaagtttgt cgggggagcc gagaacactg cccaccccg gatcatctct gcacctgaga    1320
tgagacagga gtctgagcag ggcccctgcc gcagacacat ggaggcttcc ctgcaggagc   1380
tcaaagccag cccacgcatg gtgccccgtg ctgtgtacct gcccaattgt gaccgcaaag   1440
gattctacaa gagaaagcag tgcaaaacct tcccgtggccg caaacgtggc atctgctggt  1500
gcgtggacaa gtacgggatg aagctgccag gcatggagta cgttgacggg gactttcagt   1560
gccacacctt cgacagcagc aacgttgagt gatgcgtccc cccccaacct ttccctcacc    1620
ccctcccacc cccagccccg actccagcca gcgcctccct ccaccccagg acgccactca   1680
tttcatctca tttaagggaa aaatatatat ctatctattt gaggaaactg aggacctcgg   1740
aatctctagc aagggctcaa cttcgaaaat ggcaacaaca gagatgcaaa aagctaaaaa   1800
gacacccccc cccttttaaat ggttttcttt ttgaggcaag ttggatgaac agagaaggga   1860
agagaggaag aacgagagga agagaaggga aggaagtgtt tgtgtagaag agagagaaag   1920
acgaatagag ttaggaaaag gaagacaagc aggtgggcag gaaggacatg caccgagacc   1980
aggcaggggc ccaactttca cgtccagccc tggcctgggg tcgggagagg tgggcgctag   2040
aagatgcagc ccaggatgtg gcaatcaatg acactattgg ggtttcccag gatggattgg   2100 tcaggggggag aaaggaaaag gcaaaacact ccaggacctc tcccggatct gtctcctcct   2160
ctagccagca gtatggacag ctggacccct gaacttcctc tcctcttacc tgggcagagt   2220
gttgtctctc cccaaattta taaaaactaa aatgcattcc attcctctga agcaaaaca    2280 aattcataat tgagtgatat taaatagaga ggttttcgga agcagatctg tgaatatgaa   2340
atacatgtgc atatttcatt ccccaggcag acattttta gaaatcaata catgccccaa    2400
tattggaaag acttgttctt ccacggtgac tacagtacat gctgaagcgt gccgtttcag   2460
ccctcattta attcaatttg taagtagcgc agcagcctct gtggggagg ataggctgaa    2520 aaaaaaagt gggctcgtat ttatctacag gactccatat agtcatatat aggcatataa    2580
atctattctt tttctttgtt tttttcttc ttcctttctt tcaaaggttt gcattaactt     2640
ttcaaagtag ttcctatagg ggcattgagg agcttcctca ttctgggaaa actgagaaaa   2700
cccatattct cctaatacaa cccgtaatag catttttgcc tgcctcgagg cagagttttcc   2760 cgtgagcaat aaactcagct tttttgtggg gcacagtact ggatttgaca gtgattcccc   2820
acgtgtgttc atctgcaccc accgagccag gcagaggcca gccctccgtg gtgcacacag   2880
cacgcgcctc agtccatccc attttagtct ttaaaccctc aggaagtcac agtctccgga   2940
caccacacca catgagccca acaggtccac gatggatcca ccagtcccac cccagccttt   3000
tcctttcatc tgaacagaat gtgcattttt ggaagcctcc ctcactctcc atgctggcag   3060
agcaggaggg agactgaagt aagagatggc agagggagat ggtggcaaaa aggtttagat   3120
gcaggagaac agtaagatgg atggttccgg ccagagtcga tgtggggagg aacagagggc   3180 tgaaggggaga gggggctgac tgttccattc tagctttggc acaaagcagc agaaaggggg   3240
aaaagccaat agaaatttcc ttagcttccc caccatatgt attttctagg atttgagagg   3300
aaagagagga aaatggggga atgggttgca aaatagaaat gagcttaatc caggccgcag   3360
agccagggaa ggtgagtaac tttaggaggg tgctagactt tagaagccag ataggaagaa   3420
tcagtctaaa ctggccatgc tttggaaggg acaagactat gtgctccgct gcccaccttc   3480
```

```
agcctgcaat gagggactga ggcccacgag tctttccagc tcttcctcca ttctggccag    3540
tccctgcatc ctccctgggg tggaggatgg aaggaaagct gggacaagca gggaacgcat    3600
gattcaggga tgctgtcact cggcagccag attccgaaac tcccattctc caatgacttc    3660
ctcaaccaat gggtggcctt gtgactgttc tttaaggctg aagatatcca ggaaaggggg    3720
cttggacact ggccaaggag acccttcgt gctgtggaca cagctctctt cactcttgc     3780 tcatggcatg acacagcgga gaccgcctcc aacaacgaat tggggctac gaagaggaat    3840 agcgaaaaag caaatctgtt tcaactgatg ggaaccctat agctatagaa cttggggct    3900 atctcctatg cccctggaca ggacagttgg ctggggacag gagaagtgct caatcttcat    3960
gagacaaagg ggcccgatag ggccagcagc cacaaggcct tgacctgccg agtcagcatg    4020
ccccatctct ctgcacagct gtcccctaaa cccaactcac gtttctgtat gtcttaggcc    4080
agtatcccaa acctcttcca cgtcactgtt ctttccaccc attctccctt tgcatcttga    4140
gcagttatcc aactaggatc tgccaagtgg atactggggt gccactcccc tgagaaaaga    4200
ctgagccagg aactacaagc tccccccaca ttcctcccag cctggaccta attcttgaga    4260
ggggctctct cttcacggac tgtgtctgga cttttgagcag gcttctgccc cttgcgttgg    4320
ctctttgctg ccagccatca ggtgggggat tagagcctgg tgtaagtgcg ccagactctt    4380
ccggtttcca aagttcgtgc ctgcgaaccc aaacctgtga gtctcttctg catgcaggag    4440
tttctcctgg gcagctggtc actccccaga gaagctgggc cttcatggac acatggaact    4500
aagcctccca aatgggagtt ctggctgagc ccagggtggg gagatcctgg gaagggaggc    4560
actggaggaa gacggcacct cttcccccat ggcagggtgt gagggaggca ggtttggaat    4620
ggtgcgagta tggcaatcta agcagggggtc tggtctcttt gactccaggc tggcctttgg    4680
ccgactgtct gctcacccag agaccttgga ctccggacta ccatggctc cgaatctaag    4740 tgctgcccac tccatgctc acaccacag aaggtcttcc catccccttt agattcgtgc     4800
ctcactccac cagtgaggaa gatgcctctg tctttcccac gactgccagg agataggaa    4860 gcccagccag gactgaccct ccttcctcca gcctgccctg acccacctgg caaagcaggg    4920
cacatgggga ggaagagact ggaacctttc tttgacagcc aggcctagac agacaggcct    4980
ggggacactg gccccatgag gggaggaagg caggcgcacg aggtccaggg aggcccttt    5040 ctgatcatgc cccttctctc ccaccccatc tccccaccac cacctctgtg gcctccatgg    5100
tacccccaca gggctggcct cccctagagg gtgggcctca accacctgct cccgccacgc    5160
accggttagt gagacagggc tgccacggca accgccaagc cccctcaag gtgggacagt     5220 accccggacc catccactca ctcctgagag ggctccggcc cagaatggga acctcagaga    5280
agagctctaa ggagaagaaa ccccatagcg tcagagagga tatgtctggc ttccaagaga    5340
aaggaggctc cgttttgcaa agtggaggag ggacagggga caggggtttc accagccagc    5400
aacctgggcc ttgtactgtc tgtgttttta aaaccactaa agtgcaagaa ttacattgca    5460
ctgtttctcc acttttatt ttctcttagg cttttgtttc tatttcaaac atactttctt      5520
ggttttctaa tggagtatat agtttagtca tttcacagac tctggcctcc tctcctgaaa    5580
tccttttgga tggggaaagg gaaggtgggg agggtccgag gggaagggga ccccagcttc    5640
cctgtgcccg ctcaccccac tccaccagtc cccggtcgcc agccggagtc tcctctctac    5700
cgccactgtc acaccgtagc ccacatggat agcacagttg tcagacaaga ttccttcaga    5760
ttccgagttg cctaccggtt gttttcgttg ttgttgttgt tgttttcttt tttctttttt    5820
tttttgaaga cagcaataac cacagtacat attactgtag ttctctatag ttttacatac    5880
```

```
attcatacca taactctgtt ctctcctctt ttttgttttc aactttaaaa acaaaaataa    5940
acgatgataa tctttactgg tgaaaaggat ggaaaaataa atcaacaaat gcaaccagtt    6000
tgtgagaaaa aaaaaaaaaa gccgaaaaaa aaaaaaaaaa cacctgaatg cggaagagct    6060
cggctcccgt ttagcatttt gtacttaagg aaataaaaaa ccaacaaagg atctcacatt    6120
ttcttaaaaa gtgaagattg ctgtatacta tttattcaac ttataattta tgttactcct    6180
tgatctttgt cttttgtcat gacaaagcat ttatttaata aagttatgca ttcagttaaa    6240
aaaaaaaaaa aaaaaaaaaa aaaaaaaaaa aaaaaaaaaa aaaaaaaaaa aaaaaaaaaa    6300
aaaaaaaaaa aaaaaa                                                    6316

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
gtctttgcac gcctcggtca                                                  20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
attctggagt ctttgcacgc                                                  20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
gtcttcatca tgcctccaat                                                  20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotid

<400> SEQUENCE: 57
tctcccaggt cagcagcagc                                                  20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
tctggtcccc caggacctgc                                                  20

<210> SEQ ID NO 59
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 59
ggagctcatt gtctgagacc                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
acttacttcc ctgattggac                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
aatttcctta ttgacgtact                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
gtctttatct gtttcacccc                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
gggcatcctc tttcttcttc                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
atttagggca tcctctttct                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
ttccctggtc tcatttaggg                                              20
```

```
<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
tgtctctgat tccctggtct                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotid

<400> SEQUENCE: 67
gggagctcct tcagctttgt                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
cccagagggc catcatggtc                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
ctcttcccag agggccatca                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
tcaggcaggg cttacactct                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gtgcgtagaa cttcatgcag                                              20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide
```

-continued

<400> SEQUENCE: 72
ggcggccaac caggcctgag                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
tggcggccaa ccaggcctga                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
actcctcaag ctggcggcca                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
agtagaaggg cgagctctgg                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
ttcatccaga agtagaaggg                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
cagcagggag tcgatgcggt                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
gctgccggtc gttctccagc                                              20

<210> SEQ ID NO 79
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 79
catccagcat gtgcgtctgc                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
gacatccagc atgtgcgtct                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
gtggtcctgc atgacatcca                                              20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
aagtggtcct gcatgacatc                                              20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ctggaagagc tcgtctatga                                              20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
tgtcctggaa gagctcgtct                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
gaacctgtcc tggaagagct                                              20
```

```
<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
ggaaagaaga agtgaggcct                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
gggcatcaag ctgcggacga                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
ctcaaggaag ggctggaaca                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
tctcaaggaa gggctggaac                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
tgtatcatct caaggaaggg                                              20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
gctgtggaag tggatgtcca                                              20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 92
attctgttgg cgggtgctgg                                              20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
tatgaattct gttggcgggt                                              20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
ggatctcccg gcacacagtc                                              20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
cggatctccc ggcacacagt                                              20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
gtggagttgt ggcggatctc                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
gtccttcatc cgcaggcagc                                              20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
acagtccaca gacaagatct                                              20

<210> SEQ ID NO 99
<211> LENGTH: 20
```

-continued

<212> TYPE: DNA
<213> ORGANISM: Artificial Sequence
<220> FEATURE:
<223> OTHER INFORMATION: Antisense Oligonucleotide

<400> SEQUENCE: 99
ggagggattc gtcgagctcc                                              20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
atcttccact ggtaggactt                                              20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
tgttgagcat cttccactgg                                              20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
agctgctcca gcaaggagga                                              20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
gctcgttcag ctgctccagc                                              20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
ttgccagccg ggacacccag                                              20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
cgcagatagt actggtcttc                                              20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
accgtggtga cccgcagata                                              20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
gtgatgggat cagagtcaaa                                              20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
ggagacttct acagggaccg                                              20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
gccacggtct ccataaattt                                              20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
gcaaaagcaa catccacatc                                              20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
tagagtgcag gatccagagc                                              20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 112
attagttgca tgcaggagca                                              20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
cgagatagag ccactgtacg                                              20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
gttgttggtg gaacagtcca                                              20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
tgcttaccgg tgcttttttgc                                             20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
acatctcact cctcccggtg                                              20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
aaaaagagga ccctccaagc                                              20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
tgtgtcccct tttcacctgg                                              20

<210> SEQ ID NO 119
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 119
attaccaatg gagcatggca                                              20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
caacatggcc aaaccccatg                                              20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
gcggcaggtc tccaggtctc                                              20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
ttcccttcgg agagtagaga                                              20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
tgcttgggaa atgcctgcaa                                              20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
agctggatgc cagaaaggcc                                              20

<210> SEQ ID NO 125
<211> LENGTH: 21
<212> TYPE: DNA
<213> ORGANISM: Artificial Sequence
<220> FEATURE:
<223> OTHER INFORMATION: IGFBP2 Antisense

<400> SEQUENCE: 125
gcagcccact ctcggcagca t                                            21
```

```
<210> SEQ ID NO 126
<211> LENGTH: 21
<212> TYPE: DNA
<213> ORGANISM: Artificial Sequence
<220> FEATURE:
<223> OTHER INFORMATION: IGFBP2 Antisense

<400> SEQUENCE: 126
cgcccagtag cagcagcagc a                                              21

<210> SEQ ID NO 127
<211> LENGTH: 21
<212> TYPE: DNA
<213> ORGANISM: Artificial Sequence
<220> FEATURE:
<223> OTHER INFORMATION: IGFBP2 Antisense

<400> SEQUENCE: 127
tcccggaaca cggccagctc c                                              21

<210> SEQ ID NO 128
<211> LENGTH: 18
<212> TYPE: DNA
<213> ORGANISM: Mus musculus
<220> FEATURE:
<223> OTHER INFORMATION: antisense IGFBP-5 oligodeoxynucleotide

<400> SEQUENCE: 128
gaccacgctg atcaccat                                                  18

<210> SEQ ID NO 129
<211> LENGTH: 18
<212> TYPE: DNA
<213> ORGANISM: Homo sapiens
<220> FEATURE:
<223> OTHER INFORMATION: antisense IGFBP-5 oligodeoxynucleotide

<400> SEQUENCE: 129
cgcggtgagc aacaccat                                                  18

<210> SEQ ID NO 130
<211> LENGTH: 18
<212> TYPE: DNA
<213> ORGANISM: Homo sapiens
<220> FEATURE:
<223> OTHER INFORMATION: antisense IGFBP-5 oligodeoxynucleotide

<400> SEQUENCE: 130
aggtcatgca gcagccgc                                                  18

<210> SEQ ID NO 131
<211> LENGTH: 18
<212> TYPE: DNA
<213> ORGANISM: Homo sapiens
<220> FEATURE:
<223> OTHER INFORMATION: antisense IGFBP-5 oligodeoxynucleotide

<400> SEQUENCE: 131
tcaaatagat agatatat                                                  18

<210> SEQ ID NO 132
<211> LENGTH: 21
<212> TYPE: DNA
<213> ORGANISM: artificial
<220> FEATURE:
<223> OTHER INFORMATION: antisense IGFBP-5 oligodeoxynucleotide
```

<400> SEQUENCE: 132
cgcagtgcac gaaggagccc a                                              21

<210> SEQ ID NO 133
<211> LENGTH: 21
<212> TYPE: DNA
<213> ORGANISM: artificial
<220> FEATURE:
<223> OTHER INFORMATION: RNAi for Homo sapiens IGFBP-2 and -5

<400> SEQUENCE: 133
ggagccgggc ugcggcugct t                                              21

<210> SEQ ID NO 134
<211> LENGTH: 21
<212> TYPE: DNA
<213> ORGANISM: artificial
<220> FEATURE:
<223> OTHER INFORMATION: RNAi for Homo sapiens IGFBP-2 and -5

<400> SEQUENCE: 134
gcagccgcag cccggcucct t                                              21

<210> SEQ ID NO 135
<211> LENGTH: 19
<212> TYPE: DNA
<213> ORGANISM: artificial
<220> FEATURE:
<223> OTHER INFORMATION: RNAi for Homo sapiens IGFBP-2 and -5

<400> SEQUENCE: 135
cgugcggcgu cuacacctt                                                 19

<210> SEQ ID NO 136
<211> LENGTH: 19
<212> TYPE: DNA
<213> ORGANISM: artificial
<220> FEATURE:
<223> OTHER INFORMATION: RNAi for Homo sapiens IGFBP-2 and -5

<400> SEQUENCE: 136
gguguagacg ccgcacgtt                                                 19

<210> SEQ ID NO 137
<211> LENGTH: 18
<212> TYPE: DNA
<213> ORGANISM: artificial
<220> FEATURE:
<223> OTHER INFORMATION: RNAi for Homo sapiens IGFBP-2 and -5

<400> SEQUENCE: 137
ccaggggcug cgcugctt                                                  18

<210> SEQ ID NO 138
<211> LENGTH: 18
<212> TYPE: DNA
<213> ORGANISM: artificial
<220> FEATURE:
<223> OTHER INFORMATION: RNAi for Homo sapiens IGFBP-2 and -5

<400> SEQUENCE: 138
gcagcgcagc cccuggtt                                                  18

<210> SEQ ID NO 139
<211> LENGTH: 18

```
<212> TYPE: PRT
<213> ORGANISM: Homo sapiens

<400> SEQUENCE: 139

Leu Phe Tyr Asn Glu Gln Gln Glu Ala Arg Gly Val His Thr Gln Arg
1               5                   10                  15

Met Gln
```

TREATMENT OF CANCER BY INHIBITION OF IGFBPS AND CLUSTERIN

This application is continuation-in-part of U.S. patent application Ser. No. 10/346,493, filed Jan. 17, 2003, which claims the benefit of U.S. Provisional Application No. 60/350,046 filed Jan. 17, 2002. This application also claims the benefit of U.S. Provisional Applications 60/522,948 filed Nov. 23, 2004 and 60/522,960 filed Nov. 24, 2004. All of these applications are incorporated herein by reference.

FIELD OF THE INVENTION

The present application relates to a method for treating cancer in a mammalian subject using a combination of therapeutic agents, one of which is an oligonucleotide effective to reduce the amount of clusterin, also known as testosterone-repressed prostate message-2 (TRPM-2) in the cancer cells, and the other of which reduces expression of insulin-like growth factor binding protein 2 (IGFBP-2) and/or insulin-like growth factor binding protein 5 (IGFBP-5), and also stimulates the expression of clusterin as a consequence of its action on the target. By way of non-limiting example, the agent that reduces IGFBP-2 and/or IGFBP-5 may be a bispecific antisense that inhibits IGFBP-2 and IGFBP-5 expression.

BACKGROUND OF THE INVENTION

After lung cancer, breast cancer is the second leading cause of cancer deaths in women. According to the World Health Organization, more than 1.2 million people will be diagnosed with breast cancer this year worldwide, and The American Cancer Society estimates that in 2004, over 200,000 women in the United States will be diagnosed with invasive breast cancer (Stages I-IV), and about 40,000 women and almost 500 men will die from breast cancer in the United States in 2004.

Prostate cancer is the most common cancer that affects men, and the second leading cause of cancer deaths in men in the Western world. Because prostate cancer is an androgen-sensitive tumor, androgen withdrawal, for example via castration, is utilized in some therapeutic regimens for patients with advanced prostate cancer. Androgen withdrawal leads to extensive apoptosis in the prostate tumor, and hence to a regression of the disease. However, castration-induced apoptosis is not complete, and a progression of surviving tumor cells to androgen-independence ultimately occurs. This progression is the main obstacle to improving survival and quality of life, and efforts have therefore been made to target androgen-independent cells. These efforts have focused on non-hormonal therapies targeted against androgen-independent tumor cells, however as of a 1998 report, no non-hormonal agent had improved survival. Oh et al., J. Urol 160: 1220-1229 (1998) Alternative approaches are therefore indicated.

Ovarian cancer is the seventh most common cancer and the fourth leading cause of death after lung and bronchus, breast, and colorectal cancers among U.S. women. A woman's risk of getting ovarian cancer during her lifetime is about 1 in 58. The risk of getting this cancer and dying from it is 1 in 98.

Colorectal cancer, a diagnosis which comprises both cancer of the colon and the associated rectal region, is the second leading cause of cancer death in the U.S.

Standard treatments for these various cancers include surgery, radiation, chemotherapy and hormonal therapies. Each of these treatments has drawbacks including surgical risks, illness and loss of productivity associated with radiation or chemotherapy, reproductive and hormonal side effects, and unreliable survival rates.

Thus cancer is a serious disease, fatal in many cases, and requires improved treatments to reduce fatalities and prevalence.

Clusterin or "TRPM-2" is a ubiquitous protein, with a diverse range of proposed activities. In prostate epithelial cells, expression of clusterin increases immediately following castration, reaching peak levels in rat prostate cells at 3 to 4 days post castration, coincident with the onset of massive cell death. These results have led some researchers to the conclusion that clusterin is a marker for cell death, and a promoter of apoptosis. On the other hand, Sertoli cells and some epithelial cells express high levels of clusterin without increased levels of cell death. Sensibar et al., (1995)[1] reported on in vitro experiments performed to more clearly elucidate the role of clusterin in prostatic cell death. The authors used LNCaP cells transfected with a gene encoding clusterin, and observed whether expression of this protein altered the effects of tumor necrosis factor α (TNFα), to which LNCaP cells are very sensitive. Treatment of the transfected LNCaP cells with TNFα resulted in a transient increase in clusterin levels for a few hours, but these levels had dropped by the time DNA fragmentation preceding cell death was observed.

United States published patent application US 20030166591 discloses the use of antisense therapy which reduces the expression of clusterin for the treatment of cancer of prostate and renal cell cancer. Seq. ID Nos. 4, 5, and 12 herein are shown in this reference to be operative for the stated purpose of reducing the expression of clusterin, and are identified in the reference as Seq. ID Nos. 4, 5, and 12, respectively.

U.S. Pat. No. 6,383,808 discloses compositions, particularly oligonucleotides, and methods for modulating the expression of clusterin. Seq. ID Nos. 54-123 herein are shown in this reference to be operative for the stated purpose of modulating the expression of clusterin, and are identified in U.S. Pat. No. 6,383,808 as Seq. ID Nos. 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 69, 70, 71, 72, 73, 74, 76, 78, 79, 80, 82, 83, 84, 85, 86, 87, 88 and 89, respectively.

United States published patent application 2004096882 discloses RNAi therapeutic probes targeting cancer associated proteins including clusterin. Seq. ID Nos. 36, 37, and 22-43 herein are shown in this reference to be operative to reduce clusterin, and are identified in United States published patent application 2004096882 as Seq. ID Nos. 1-16, 58, 59, 61, 62, 64, 65, 67, and 68, respectively.

United States published patent application US2004053874 discloses antisense modulation of clusterin expression. Seq. ID Nos. 54-123 herein are shown in this reference to be operative for the purpose of modulating the expression of clusterin, and are identified in United States published patent application US2004053874 as Seq. ID Nos. 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 69, 70, 71, 72, 73, 74, 76, 78, 79, 80, 82, 83, 84, 85, 86, 87, 88 and 89, respectively.

United States published patent application US 2003166591 discloses clusterin antisense therapy using an oligonucleotide having 2'-O-(2-methoxy)ethyl modifications. Seq. ID Nos. 4, 5, and 12 herein are shown in United States published patent application US 2003166591 to be operative for reducing the expression of clusterin, and are identified in United States published patent application US 2003166591 as Seq. ID Nos. 4, 5, and 12, respectively.

United States published patent application US 2003158130 discloses the use of chemotherapy-sensitization and radiation-sensitization of cancer by antisense clusterin oligodeoxynucleotides. Seq. ID Nos. 4, 5, and 12 herein are shown in United States published patent application US 2003158130 to be operative for reducing the expression of clusterin, and are identified in United States published patent application US 2003158130 as Seq. ID Nos. 4, 5, and 12, respectively.

SUMMARY OF THE INVENTION

Applicants have found that agents that reduce the amount of IGFBP-2 and/or IGFBP-5 and that are known to be useful in the treatment of cancer result in increased expression of the protein clusterin. Since clusterin can provide protection against apoptosis, this secondary effect detracts from the efficacy of the therapeutic agent. In overcoming this, the present invention provides a combination of therapeutic agents that is useful in the treatment of cancer. The combination comprises an agent that reduces the amount of IGFBP-2 and/or IGFBP-5 and that stimulates expression of clusterin as a secondary effect, and an oligonucleotide that is effective to reduce the amount of clusterin in cancer cells. In some embodiments of the invention, the agent that reduces IGFBP-2 and/or IGFBP-5 is a bispecific antisense species. The oligonucleotide may be an antisense oligonucleotide or an RNAi oligonucleotide.

The combination of the invention is useful in a method for treating cancer in a mammalian subject, comprising administering to the subject the agent that reduces IGFBP-2 and/or IGFBP-5 and an oligonucleotide effective to reduce the amount of clusterin in the cancer cells.

The cancer may be breast cancer, osteosarcoma, lung cancer, pancreatic cancer, salivary gland cancer, colon cancer, prostate cancer, endometrial cancer, and bladder, for example.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION OF THE INVENTION

Definitions

Definition and Sequences for IGFBP 2/5

Figure 1A:
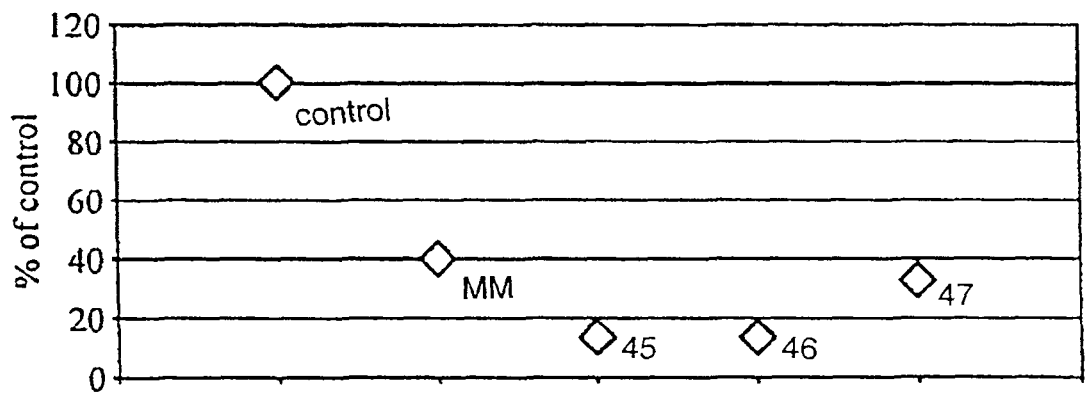
FIG. 1 the amount of IGBFP-2 and IGBFP-5 expression observed in LNCaP and PC3 cells, respectively, upon administration of one of three bispecific antisense oligonucleotides, a mismatch control (MM), or no olignucleotide (control).

As used in the specification and claims of this application, the terms "insulin-dependent growth factor-2" and "IGFBP-2" are used interchangeably. The nucleotide sequence of human IGFBP-2 is known from NCBI sequence accession no. NM_000597 and is set forth in Seq. ID No. 52.

As used in the specification and claims of this application, the terms "insulin-dependent growth factor-5" and "IGFBP-5" are used interchangeably. The nucleotide sequence of human IGFBP-2 is known from NCBI sequence accession no. NM_000599 and is set forth in Seq. ID No. 53.

As used in the specification and claims of this application, the term "clusterin" refers to the glycoprotein originally derived from ram rete testes, and to homologous proteins derived from other mammalian species, including humans, whether denominated as clusterin or an alternative name. The sequences of numerous clusterin species are known. For example, the sequence of human clusterin is reported by Wong et al., (1994) [2], and in NCBI sequence accession number NM_001831 and is set forth in Seq. ID No.: 1. In this sequence, the coding sequence spans bases 48 to 1397.

As used in this application, the term "amount of clusterin" refers to the amount of clusterin which is present in a form which is functional to provide anti-apoptotic protection. The effective amount of clusterin may be reduced through restricting production of clusterin (at the transcription or translation level) or by degrading clusterin at a rate faster than it is being produced. Further, it will be appreciated that inhibition occurs when the clusterin would otherwise be present if the antisense oligonucleotide had not been administered.

As used in this application, the term "amount of IGFBP-2 and/or IGFBP-5" refers to the amount of the binding protein which is present.

As used in the specification, "antisense oligonucleotide" refers to stretches of single-stranded DNA, usually chemically modified, whose sequence (3'→5') is complementary to the sense sequence of a molecule of mRNA. Antisense molecules thereby effectively inhibit gene expression by forming RNA/DNA duplexes, and offer a more targeted option for cancer therapy than chemotherapy or radiation. Antisense is believed work by a variety of mechanisms, including physically blocking the ability of ribosomes to move along the messenger RNA, and hastening the rate at which the mRNA is degraded within the cytosol. The abbreviation ASO may also be used to refer to an antisense oligonucleotide As used in the specification and claims of this application, the term "combination" refers to an assemblage of reagents for use in therapy either by simultaneous or contemporaneous administration. Simultaneous administration refers to administration of an admixture (whether a true mixture, a suspension, an emulsion or other physical combination) of the agent that reduces IGFBP-2 and/or IGFBP-5 and the oligonucleotide. In this case, the combination may be the admixture or separate containers of the agent and the oligonucleotide that are combined just prior to administration. Contemporaneous administration refers to the separate administration of the agent and the oligonucleotide at the same time, or at times sufficiently close together that a enhanced or synergistic activity relative to the activity of either the agent or the oligonucleotide alone is observed. In this, the combination comprises separate containers of the agent and the oligonucleotide Agents that Reduce IGFBP-2 and/or IGFBP-5

The agent used in the combinations and method of the present invention is one that reduced the amount of IGFBP-2 and/or IGFBP-5.

In one embodiment of the invention, this agent is a bispecific agent complementary to portions of the IGFBP-2 and/or IGFBP-5 gene or mRNA, wherein substantially all of the oligodeoxynucleotide consists essentially of a sequence of bases that is complementary to a portion of portions of a gene encoding human IGFBP-2 and substantially all of the oligodeoxynucleotide is also complementary to a gene encoding human IGFBP-5, and wherein the oligodeoxynucleotide which is of sufficient length (in general at least 15 bases) to act as an antisense inhibitor of the effective amount of human IGFBP-2 and human IGFBP-5. Specific bispecific antisense oligonucleotides of this type that can be used as the agent in the invention consist essentially of a series of bases as set forth in Seq. ID. No. 45 through 51 as follows:

```
                              Seq ID No.: 45
ggtgtagacgccgcacg

Seq ID No.: 46
gcagcgcagccctgg

Seq ID No.: 47
gcagcagccgcagcccggctcc

Seq ID No.: 48
agccgcagcccggctcct

Seq ID No.: 49
cagcagccgcagcccggctc

Seq ID No.: 50
gcagcagccgcagcccggct

Seq ID No.: 51
agcagccgcagcccggctcc
```

These antisense oligonucleotides employed may be modified to increase the stability of the antisense oligonucleotide in vivo. For example, the antisense oligonucleotides may be employed as phosphorothioate derivatives (replacement of a non-bridging phosphoryl oxygen atom with a sulfur atom) which have increased resistance to nuclease digestion. Increased antisense oligonucleotide stability can also be achieved using molecules with 2-methoxyethyl (MOE) substituted backbones as described generally in U.S. Pat. No. 6,451,991 and U.S. patent application Ser. No. 10/080,794 which are incorporated herein by reference. Seq. ID Nos. 4, 5, and 12 herein are shown in U.S. patent application Ser. No. 10/080,794 to be operative for reducing the expression of clusterin, and are identified in U.S. patent application Ser. No. 10/080,794 as See. ID Nos. 45 and 12 respectively.

Reduction in the amount of IGFBP-2 and/or IGFBP-5 can be accomplished using therapeutics, alone or in combination, that target the two binding proteins individually. By way of non-limiting example, antisense species that reduce IGFBP-2 or IGFBP-5 individually are described in International Patent Publication Nos. WO02/22642 and WO01/05435, which are incorporated herein by reference. Seq. ID Nos. 125, 126, and 127 herein are shown in WO02/22642 to be operative for the stated purpose of reducing IGFBP-2, and are identified in that reference as Seq. ID Nos. 1, 2, and 3, respectively. Seq. ID Nos. 128, 129, 130, and 131 herein are shown in WO01/05435 to be operative for the stated purpose of reducing IGFBP-5, and are identified in that reference as Seq. ID Nos. 1, 3, 4, and 10, respectively. Antisense sequences are also disclosed in Huynh, Hung, et al.; "A Role for Insulin-Like Growth Factor Binding Protein 5 in the Antiproliferative Action of the Antiestrogen ICI 182782"; Cell Growth & Differentiation, Vol. 7, No. 11, pages 1501-1506; 1996. Seq. ID No. 132 herein is shown in Huynh et al. to be operative for the stated purpose of reducing IGFBP-5 accumulation.

The amount of antisense oligonucleotide administered is one effective to reduce the effective amount of levels of IGFBP-2 and/or IGFBP-5 in the tumor/cancer cell of concern. As noted above, in the context of the present invention, applicants do not intend to be bound by any specific mechanism by which this reduction may occur, although it is noted that the reduction may occur as a result of reduced expression of IGFBP-2 and -5 if the antisense molecule interferes with translation of the mRNA, or via an RNase mediated mechanism. Furthermore, it will be appreciated that the appropriate therapeutic amount will vary both with the effectiveness of the specific antisense oligonucleotide employed, and with the nature of any carrier used. The determination of appropriate amounts for any given composition is within the skill in the art, through standard series of tests designed to assess appropriate therapeutic levels The combination and method of the invention can also be practiced using siRNA molecules to reduce IGFBP-2 and/or IGFBP-5. By way of non-limiting example, antisense species that reduce IGFBP-2 or IGFBP-5 individually are described in International Patent Publication No. WO2004/018676, which is incorporated herein by reference. Seq. ID Nos. 133-138 herein are shown in WO2004/018676 to be operative for the stated purpose of reducing IGFBP-2 and/or IGFBP-5, and are identified in WO2004/018676 as Seq. ID Nos. 39-44, respectively Reduction in the amount of IGFBP-2 and/or 5 may also be obtained using a fusion protein that contains distinct regions that target the two proteins. By way of non-limiting example, such a fusion protein is disclosed in U.S. Pat. No. 5,929,040, which is incorporated herein by reference.

Other molecules that can be used to reduce the amount of IGFBP-2 and/or IGFBP-5 include therapeutic antibodies such as those described in International Patent Publication No. WO00/69454. Seq. ID No. 139 herein is shown in WO00/69454 to be operative for the purpose of generating antibodies, and is identified in WO00/69454 as Seq. ID No. 3.

Oligonucleotides

Antisense Oligonucleotides (ASO) Antisense oligonucleotides are synthetic polymers made up of monomers of deoxynucleotides like those in DNA. In the present application, the term antisense oligonucleotides includes antisense oligodeoxynucleotides.

The antisense oligonucleotides for use in the combination and method of the invention for treatment of cancer in humans may be complementary to the nucleotide sequence of human clusterin as set forth in Seq. ID No. 1. Exemplary sequences which can be employed as antisense oligonucleotides in the combination and method of the invention are disclosed in PCT Patent Publication WO 00/49937, US Patent Publication US-2002-0128220-A1, and U.S. Pat. No. 6,383,808, all of which are incorporated herein by reference in those jurisdictions where such incorporation is permitted. Seq. ID Nos. 4, 5, and 12 herein are shown in PCT Patent Publication WO 00/49937 to be operative for the purpose of reducing clusterin, and are identified in PCT Patent Publication WO 00/49937 as Seq. ID Nos. 4, 5, and 12. Seq. ID Nos. 4, 5, and 12 herein are shown in US Patent Publication US-2002-0128220-A1 to be operative for the purpose of reducing clusterin, and are identified in PCT Patent Publication US Patent Publication US-2002-0128220-A1 as Seq. ID Nos. 4, 5, and 12. Seq. ID Nos. 54-123 herein are shown in U.S. Pat. No. 6,383,808 to be operative for the purpose of inhibiting the expression of clusterin, and are identified in United States published patent application U.S. Pat. No. 6,383,808 as Sec. ID Nos. 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 69, 70, 71, 72, 73, 74, 76, 78, 79, 80, 82, 83, 84, 85, 86, 87, 88 and 89, respectively. In specific embodiments, the antisense oligonucleotide may span either the translation initiation site or the termination site of clusterin. The antisense oligonucleotide comprises and may consist essentially of an oligonucleotide selected from the group consisting of Seq. ID. Nos.: 2 to 19 as shown in Table 1, or more specifically Seq. ID. No. 4, Seq. ID. No. 5 and Seq. ID. No. 12.

TABLE 1

| Seq ID No. | Description | SEQUENCE (5' to 3') |
|---|---|---|
| 2 | Antisense TRPM-2 oligonucleotide | GCACAGCAGGAGAATCTTCAT |
| 3 | Antisense TRPM-2 oligonucleotide | TGGAGTCTTTGCACGCCTCGG |
| 4 | Antisense oligonucleotide corresponding to the human TRPM-2 translation initiation site | CAGCAGCAGAGTCTTCATCAT |
| 5 | Antisense TRPM-2 oligonucleotide | ATTGTCTGAGACCGTCTGGTC |
| 6 | Antisense TRPM-2 oligonucleotide | CCTTCAGCTTTGTCTCTGATT |
| 7 | Antisense TRPM-2 oligonucleotide | AGCAGGGAGTCGATGCGGTCA |
| 8 | Antisense TRPM-2 oligonucleotide | ATCAAGCTGCGGACGATGCGG |
| 9 | Antisense TRPM-2 oligonucleotide | GCAGGCAGCCCGTGGAGTTGT |
| 10 | Antisense TRPM-2 oligonucleotide | TTCAGCTGCTCCAGCAAGGAG |
| 11 | Antisense TRPM-2 oligonucleotide | AATTTAGGGTTCTTCCTGGAG |
| 12 | Antisense TRPM-2 oligonucleotide | GCTGGGCGGAGTTGGGGCCT |
| 13 | Antisense TRPM-2 oligonucleotide | GGTGTAGACG CCGCACG |
| 14 | Antisense TRPM-2 oligonucleotide | GCAGCGCAGC CCCTGG |
| 15 | Antisense TRPM-2 oligonucleotide | GCAGCAGCCG CAGCCCGGCT CC |
| 16 | Antisense TRPM-2 oligonucleotide | AGCCGCAGCC CGGCTCCT |

TABLE 1-continued

| Seq ID No. | Description | SEQUENCE (5' to 3') |
|---|---|---|
| 17 | Antisense TRPM-2 oligonucleotide | CAGCAGCCGC AGCCCGGCTC |
| 18 | Antisense TRPM-2 oligonucleotide | GCAGCAGCCG CAGCCCGGCT |
| 19 | Antisense TRPM-2 oligonucleotide | AGCAGCCGCAGCCCGGCTCC |
| 20 | 2 base TRPM-2 mismatch oligonucleotide used as a control | CAGCAGCAGAGTATTTATCAT |

As used in the specification and claims of this application, the phrase "consist essentially of" means that the oligonucleotide contains just the based of the identified sequence or such bases and a small number of additional bases that do not materially alter the antisense function of the oligonucleotide.

In order avoid digestion by DNAse, antisense oligonucleotides and ODNs are often chemically modified. For example, phosphorothioate oligodeoxynucleotides are stabilized to resist nuclease digestion by substituting one of the non-bridging phosphoryl oxygen of DNA with a sulfur. Increased antisense oligonucleotide stability can also be achieved using molecules with 2-methoxyethyl (MOE) substituted backbones as described generally in U.S. Pat. No. 6,451,991, incorporated by reference in those jurisdictions allowing such incorporation, and US Published patent application US-2003-0158143-A1. Seq. ID Nos. 45-51 herein are shown in US-2003-0158143-A1 to be operative for the purpose of inhibiting IGFBP-2 and IGFBP-5, and are identified in US-2003-0158143-A1 as Seq. ID Nos. 1-7, respectively. Thus, in the combination and method of the invention, the antisense oligonucleotide be modified to enhance in vivo stability relative to an unmodified oligonucleotide of the same sequence. The modification may be a (2'-O-(2-methoxyethyl) modification. The oligonucleotide may have a phosphorothioate backbone throughout, the sugar moieties of nucleotides 1-4 and 18-21 may bear 2'-O-methoxyethyl modifications and the remaining nucleotides may be 2'-deoxynucleotides.

The antisense oligonucleotide may be a 5-10-5 gap-mer methoxyl ethyl modified (MOE) oligonucleotide corresponding to SEQ ID NO.: 5 below. The antisense oligonucleotide may be from 10-25 bases in length, or from 15-23 bases in length, or from 18-22 bases in length, or 21 bases in length. A particularly preferred antisense oligonucleotide is a 21 mer oligonucleotide (CAGCAGCAGAGTCTTCATCAT; SEQ ID NO.: 4) targeted to the translation initiation codon and next 6 codons of the human clusterin sequence with a 2'-MOE modification. In one embodiment, this oligonucleotide has a phosphorothioate backbone throughout. The sugar moieties of nucleotides 1-4 and 18-21 (the "wings") bear 2'-O-methoxyethyl modifications and the remaining nucleotides (nucleotides 5-17; the "deoxy gap") are 2'-deoxynucleotides. Cytosines in the wings (i.e., nucleotides 1, 4 and 19) are 5-methylcytosines.

RNAi Oligonucleotides

Reduction in the amount of clusterin may also be achieved using RNA interference or "RNAi". RNAi is a term initially coined by Fire and co-workers to describe the observation that double-stranded RNA (dsRNA) can block gene expression[3]. Double stranded RNA, or dsRNA directs gene-specific, post-transcriptional silencing in many organisms, including vertebrates. RNAi involves mRNA degradation, but many of the biochemical mechanisms underlying this interference are unknown. The use of RNAi has been further described[3,4].

The initial agent for RNAi is a double stranded RNA molecule corresponding to a target nucleic acid. The dsRNA is then thought to be cleaved in vivo into short interfering RNAs (siRNAs) which are 21-23 nucleotides in length (19-21 bp duplexes, each with 2 nucleotide 3' overhangs). Alternatively, RNAi may be effected via directly introducing into the cell, or generating within the cell by introducing into the cell a suitable precursor (e.g. vector, etc.) of such an siRNA or siRNA-like molecule. An siRNA may then associate with other intracellular components to form an RNA-induced silencing complex (RISC).

RNA molecules used in embodiments of the present invention generally comprise an RNA portion and some additional portion, for example a deoxyribonucleotide portion. The total number of nucleotides in the RNA molecule is suitably less than 49 in order to be effective mediators of RNAi. In preferred RNA molecules, the number of nucleotides is 16 to 29, more preferably 18 to 23, and most preferably 21-23.

In certain embodiments of the invention, the siRNA or siRNA-like molecule is less than about 30 nucleotides in length. In a further embodiment, the siRNA or siRNA-like molecules are about 21-23 nucleotides in length. In an embodiment, siRNA or siRNA-like molecules comprise and 19-21 bp duplex portion, each strand having a 2 nucleotide 3' overhang.

In certain embodiments of the invention, the siRNA or siRNA-like molecule is substantially identical to a clusterin-encoding nucleic acid or a fragment or variant (or a fragment of a variant) thereof. Such a variant is capable of encoding a protein having clusterin-like activity. In some embodiments, the sense strand of the siRNA or siRNA-like molecule is targeted to the same portion of the DNA as antisense SEQ ID NO: 4 or a fragment thereof (RNA having U in place of T residues of the DNA sequence). In other embodiments, the RNAi sequence consists of Seq. Id. No. 41 or 43. For example, United States published patent application 2004096882 discloses RNAi therapeutic probes targeting clusterin. In addition, reagents and kits for performing RNAi are available commercially from for example Ambion Inc. (Austin, Tex., USA) and New England Biolabs Inc. (Beverly, Mass., USA). Suitable sequences for use as RNAi in the present invention are set forth in the present application as Seq. ID Nos. 21 to 44 as shown in Table 2.

TABLE 2

| SEQ ID No. | Description | SEQUENCE |
| --- | --- | --- |
| 21 | RNAi for human clusterin | GUAGAAGGGC GAGCUCUGGTT |
| 22 | RNAi for human clusterin | GAUGCUCAACACCUCCUCCT T |
| 23 | RNAi for human clusterin | GGAGGAGGUG UUGAGCAUCT T |
| 24 | RNAi for human clusterin | CUAAUUCAAU AAAACUGUCT T |
| 25 | RNAi for human clusterin | GACAGUUUUA UUGAAUUAGT T |

TABLE 2-continued

| SEQ ID No. | Description | SEQUENCE |
| --- | --- | --- |
| 26 | RNAi for human clusterin | UAAUUCAACA AAACUGUTT |
| 27 | RNAi for human clusterin | ACAGUUUUGU UGAAUUAUT |
| 28 | RNAi for human clusterin | AUGAUGAAGA CUCUGCUGCT T |
| 29 | RNAi for human clusterin | GCAGCAGAGU CUUCAUCAUT T |
| 30 | RNAi for human clusterin | UGAAUGAAGG GACUAACCUG TT |
| 31 | RNAi for human clusterin | CAGGUUAGUC CCUUCAUUCA TT |
| 32 | RNAi for human clusterin | CAGAAAUAGA CAAAGUGGGG TT |
| 33 | RNAi for human clusterin | CCCCACUUUG UCUAUUUCUG TT |
| 34 | RNAi for human clusterin | ACAGAGACUA AGGGACCAGA TT |
| 35 | RNAi for human clusterin | ACAGAGACUA AGGGACCAGA TT |
| 36 | RNAi for human clusterin | CCAGAGCUCG CCCUUCUACT T |
| 37 | RNAi for human clusterin | GUAGAAGGGC GAGCUCUGGT T |
| 38 | RNAi for human clusterin | GUCCCGCAUC GUCCGCAGCT T |
| 39 | RNAi for human clusterin | GCUGCGGACG AUGCGGGACT T |
| 40 | RNAi for human clusterin | CUAAUUCAAU AAAACUGUCT T |
| 41 | RNAi for human clusterin | GACAGUUUUA UUGAAUUAGT T |
| 42 | RNAi for human clusterin | AUGAUGAAGA CUCUGCUGC |
| 43 | RNAi for human clusterin | GCAGCAGAGU CUUCAUCAU |
| 44 | RNAi for human clusterin | CCAGAGCUCG CCCUUCUACT T |

Cancers that can be Treated

The combination of the present application is useful in the treatment of a variety of cancers for which IGFBP-2 and/or IGFBP-5 is considered relevant. Such cancers include without limitation endocrine-regulated tumors, for example, breast, prostate, ovarian and colon cancers. Determination of whether a given agent used in the treatment of cancer by reduction of IGFBP-2 and/or IGFBP-5 results in enhancement of clusterin expression can be readily determined using Northern blot or other techniques to detect clusterin mRNA or protein in the presence and absence of the agent. Those agents that result in enhanced clusterin expression may be made more effective through use in combination with an oligonucleotide inhibitor of clusterin expression Methods Administration of antisense ODNs can be carried out using the various mechanisms known in the art, including naked administration and administration in pharmaceutically acceptable lipid carriers. For example, lipid carriers for antisense delivery are disclosed in U.S. Pat. Nos. 5,855,911 and 5,417,978. In general, the antisense is administered by intravenous, intraperitoneal, subcutaneous or oral routes, or direct local tumor injection.

The amount of antisense ODN administered is one effective to reduce the expression of clusterin in cancer cells. It will be appreciated that this amount will vary both with the effectiveness of the antisense ODN employed, and with the nature of any carrier used. The determination of appropriate amounts for any given composition is within the skill in the art, through standard series of tests designed to assess appropriate therapeutic levels. In one embodiment, the antisense ODN is administered to a human patient in an amount of between 40-640 mg, or more particularly, from 300-640 mg. In another embodiment, the antisense ODN is administered according to the weight of the subject in need of the treatment. For example, the antisense ODN may be provided at a dosage of from 1 to 20 mg/kg of body weight.

The amount of and route of administration for the agent targeted to IGFBP-2 and/or IGFBP-5 will of course depend on the agent employed. In the case of antisense the amount administered is one effective to reduce the effective amount of levels of IGFBP-2 and/or IGFBP-5 in the endocrine-regulated tumor cell of concern. As noted above, in the context of the present invention, applicants do not intend to be bound by any specific mechanism by which this reduction may occur, although it is noted that the reduction may occur as a result of reduced expression of IGFBP-2 and -5 if the antisense molecule interferes with translation of the mRNA, or via an RNase mediated mechanism. Furthermore, it will be appreciated that the appropriate therapeutic amount will vary both with the effectiveness of the specific antisense oligonucleotide employed, and with the nature of any carrier used. The determination of appropriate amounts for any given composition is within the skill in the art, through standard series of tests designed to assess appropriate therapeutic levels.

Additional Therapeutic Agents

The method for treating cancer in accordance with one embodiment of the invention may further include administration of chemotherapy agents or other agents useful in breast cancer therapy and/or additional antisense ODNs directed at different targets in combination with the therapeutic effective to reduce the amount of active clusterin. For example, antisense clusterin ODN may be used in combination with more conventional chemotherapy agents such as taxanes (paclitaxel or docetaxel), mitoxanthrone, doxorubicin, gemcitabine, cyclophosphamide, decarbazine, topoisomerase inhibitors), angiogenesis inhibitors, differentiation agents and signal transduction inhibitors.

The application is further described in the following non-limiting examples.

EXAMPLES

Materials and Methods

Phosphorothioate oligonucleotides used in this study to target clusterin were purchased from La Jolla Pharmaceuticals Co. (La Jolla, Calif., USA) or provided by OncoGenex Technologies Inc., Vancouver, Canada. The sequence of the clusterin ASO used corresponded to the human clusterin translation initiation site (5'-CAGCAGCAGAGTCTTCAT-CAT-3') (SEQ ID NO.: 4). A 2-base clusterin mismatch oligonucleotide (5'-CAGCAGCAGAGTATTTATCAT-3') (SEQ ID NO.: 20) was used as control. Oligonucleotides were delivered into cells in form of complexes with the Lipofectin™ transfection reagent (Invitrogen). Cells were incubated with different concentrations of oligonucleotides and Lipofectin™ for 6 hours in OPTIMEM™ medium (Gibco). At the end of oligonucleotide treatment, the medium was replaced with fresh growth medium containing 2% of fetal calf serum and at different time points, cells were processed according to the various analyses to be performed.

Example 1

LNCaP cells were treated with treated with 500 nM concentrations of antisense oligonucleotides of Seq. ID Nos. 45, 46 or 47 or a mismatch control. Levels of IGFBP-2 were measured. The results are summarized in FIG. 1A.

Figure 1B:
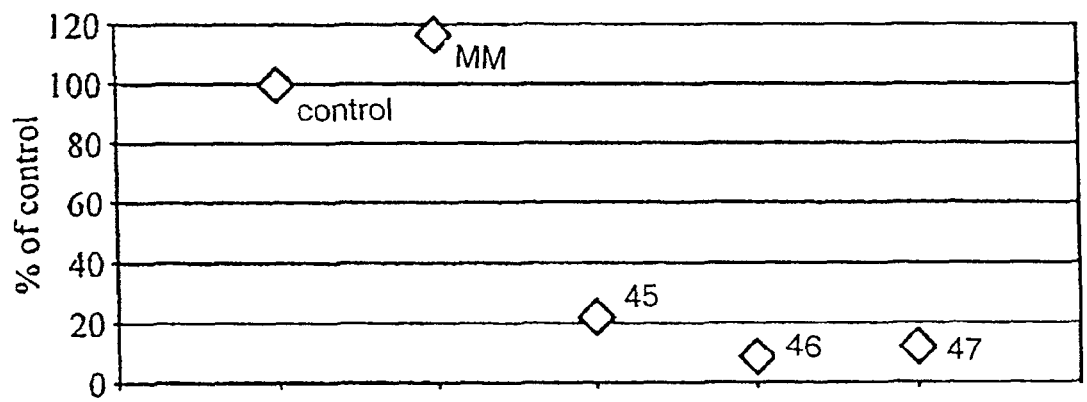

PC3 cells were treated with treated with 500 nM concentrations of antisense oligonucleotides of Seq. ID Nos. 45, 46 or 47 or a mismatch control. Levels of IGFBP-5 were measured. The results are summarized in FIG. 1B Example 2

Figure 2A:
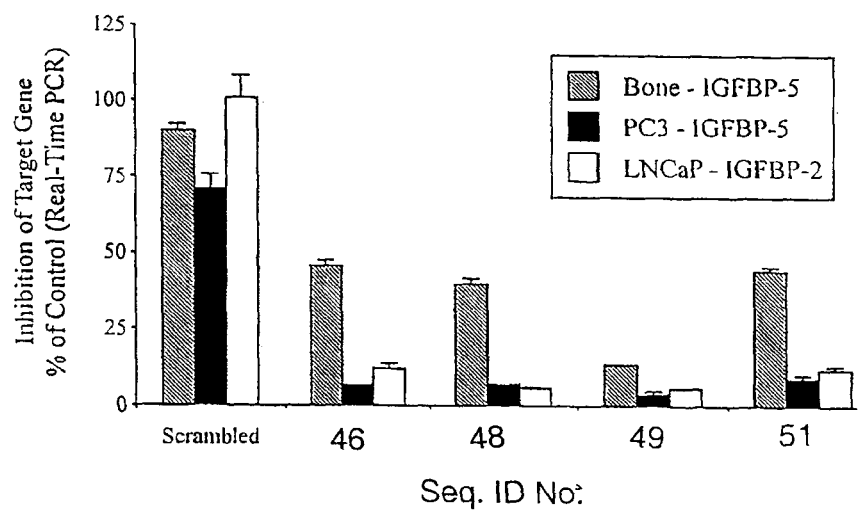
FIGS. 2A-E shows inhibition of IGFBP-2 and 5 in prostate cancer and bone cells using various antisense oligonucleotides.
Figure 2B:
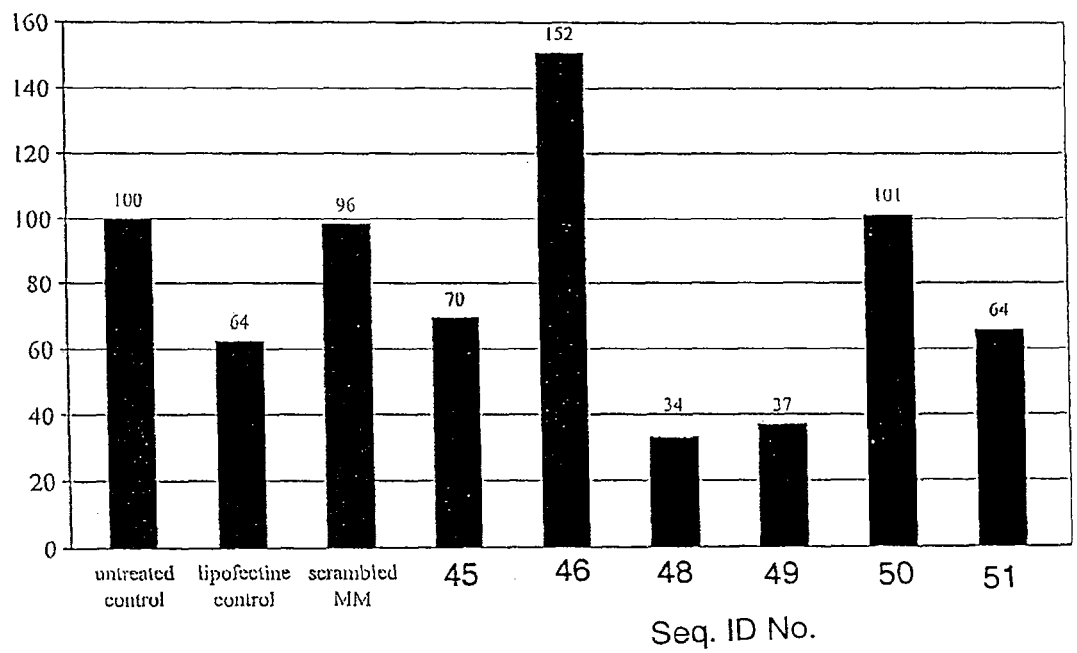
Figure 2C:
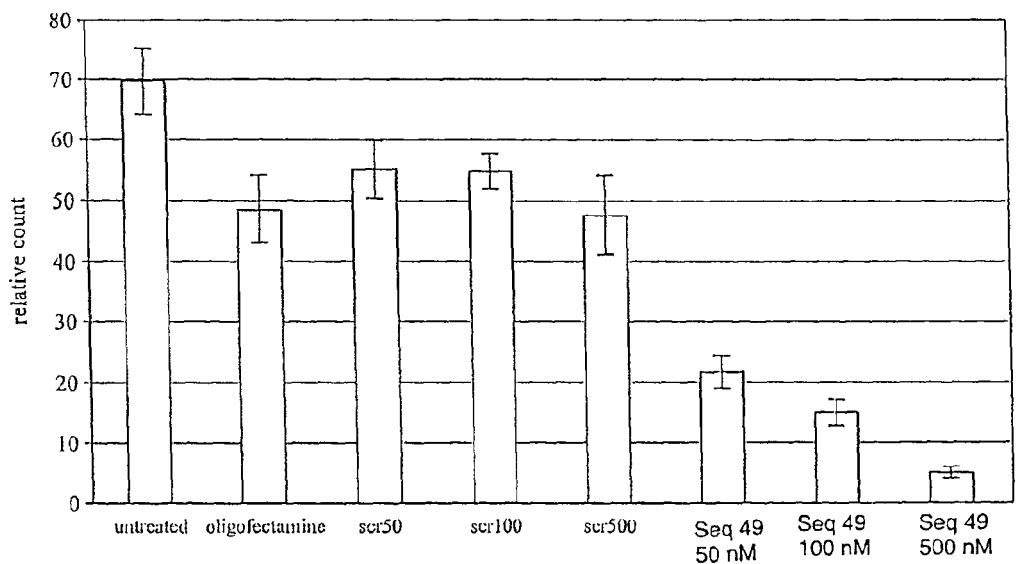
Figure 2D:
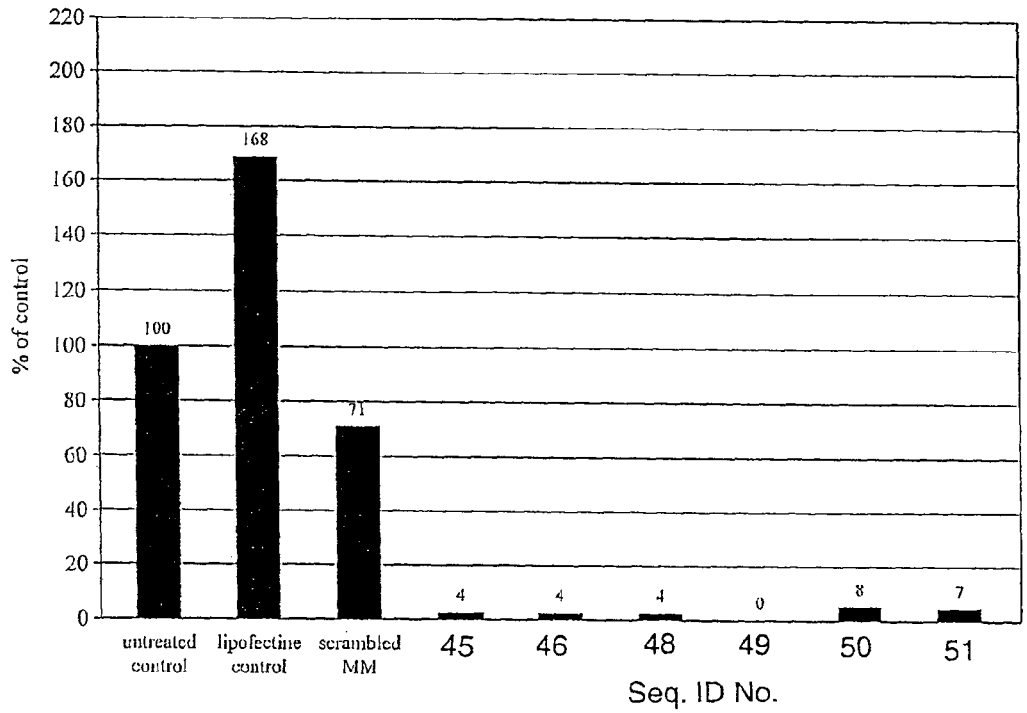
Figure 2E:
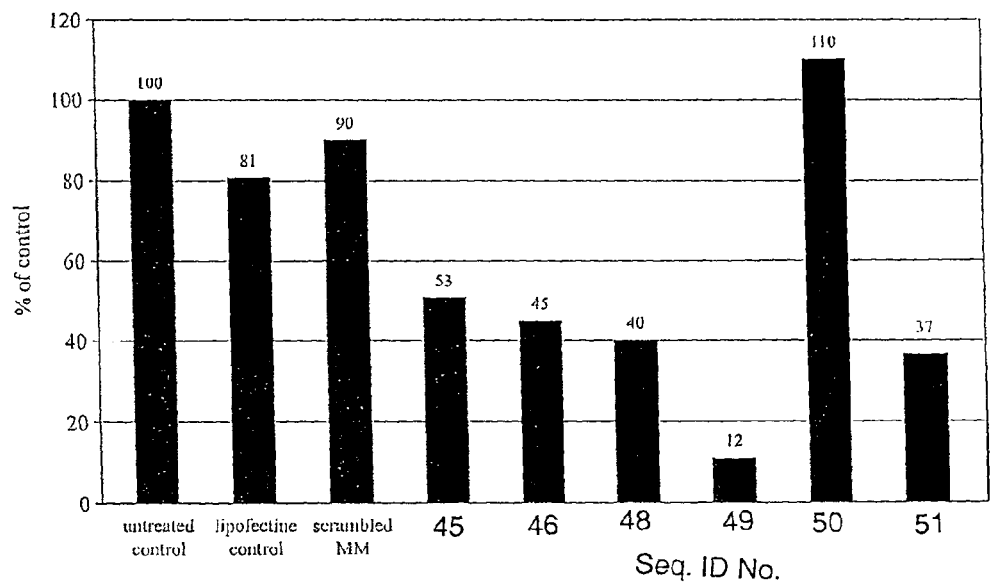

Bispecific antisense oligonucleotides were used to treat PC3, LNCaP and bone cells at concentration of 500 nm, and the amount of inhibition of IGFBP-2 or IGFBP-5 was measured using real time PCR. Oligonucleotides of Seq. ID Nos. 46, 48, 49 and 51 were tested, and all were effective to reduce the detected amount of the IGFBP measured. (FIG. 2A) Reductions of up to 70% in IGFBP-2 levels were also observed in A549 lung cells using 500 nM of Seq. ID Nos. 48 and 49. (FIG. 2B) Seq. ID No. 48 (500 nM) was also shown to be effective to inhibit cell growth of LNCaP cells and reduce the cell number by more than 90%. (FIG. 2C) FIGS. 2D and E respectively show results for inhibition of IGFBP-5 levels in PC3 cells with 500 nM of Seq ID Nos. 45, 46, 48, 49, 50 and 51; and inhibition of IGBFP-5 levels in human fetal bone fobroblast cells with 500 nM of Seq. ID Nos. 45, 46, 48, 49, 50 and 51.

Example 3

Figure 5:
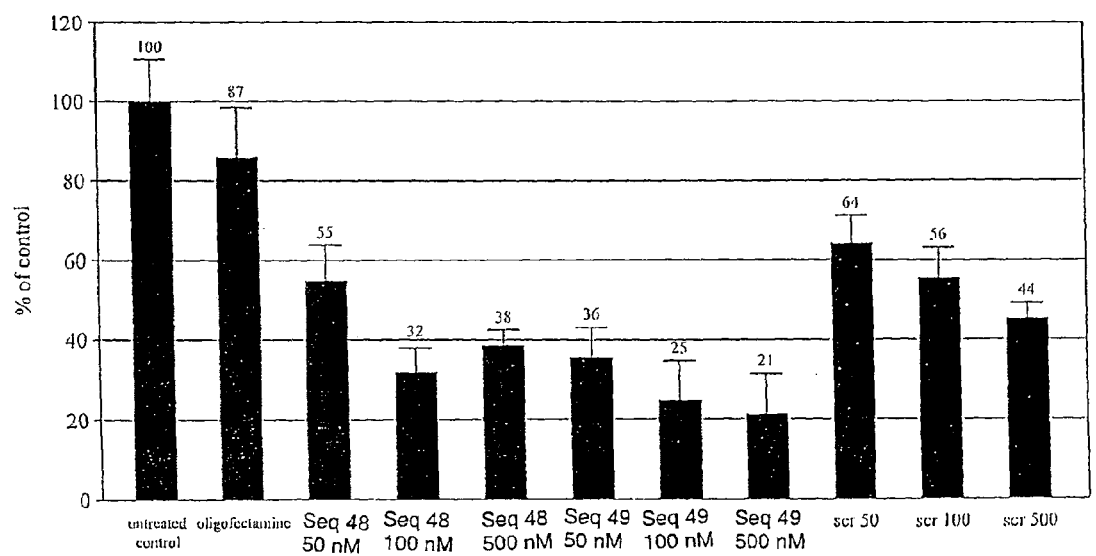
FIG. 5 shows results of real time PCR measurement of IGFBP-5 in MSF human fetal fibroblast cells after antisense treatment.

Real time PCR was used to measure the amount IGFBP-5 in MSF human fetal fibroblast cells after treatment with antisense oligonucleotide and LIPOFECTIN (4 µg/ml). Cells were plated in vitro and treated with a four-hour pulse of 500 nM oligonucleotide followed by a 20 hour period in normal medium plus 5% serum. A second four-hour pulse was repeated on day 2 and the cells were counted on day 3. The most active antisense oligonucleotides were Seq. ID Nos. 48 and 49. (FIG. 5)

Example 4

Figure 3:
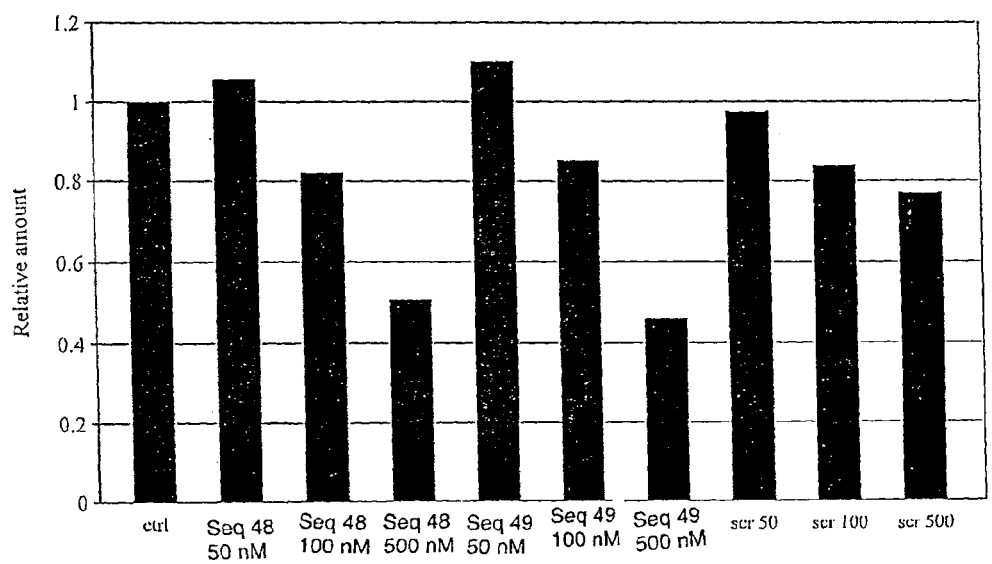
FIGS. 3 and 4 show real time PCR results for levels of IGFBP-2 and IGFBP-5 in RT4 bladder cancer cells after treatment with antisense oligonucleotides of the invention.
Figure 4:
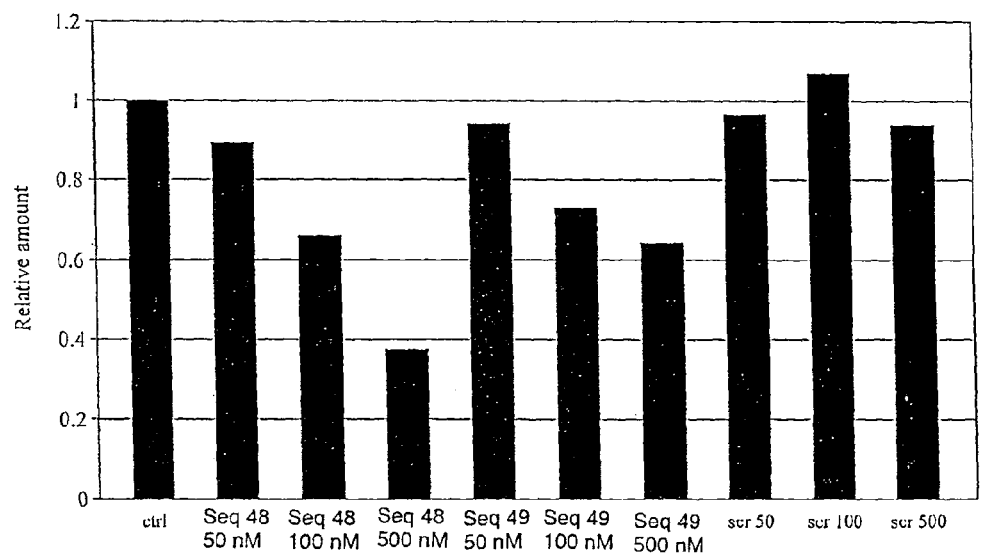

Real time PCR was used to evaluate the amounts of IGFBP-2 and IGFBP-5 in human bladder cancer (RT4) following treatment with varying amounts of antisense oligonucleotides (Seq. ID Nos. 48 and 49) and 4 µg/ml LIPOFECTIN. As shown in FIGS. 3 and 4, a dose dependent response was observed to both antisense oligonucleotides at concentrations ranging from 50 to 500 nM.

Example 5

Bispecific antisense (cagcagccgcagcccggctc, Seq. ID No. 49) targeted to IGFBP-2 and IGFBP-5 was found to induce apoptosis triggered expression of the stress-associated cytoprotective chaperone, clusterin in two prostate cancer cell lines. LNCaP and PC-3 cells were treated with the antisense and clusterin levels assessed by Western blotting. Full length clusterin was up-regulated by treatment with the bispecific antisense in PC-3 and LNCaP cells, while no significant changes were observed with control ODN. Endogenous clusterin expression in PC-3 cells increased by about 75%. Clusterin expression in LNCaP cells was almost undetectable under basal conditions, but increase >20 fold after treatment with the bispecific antisense.

Example 6

We next tested whether the bispecific antisense-induced up-regulation of clusterin could be inhibited using anti-clusterin antisense using a second generation MOE-gapmer ASO targeting the translation initiation site of clusterin (Seq. ID No. 4). PC-3 and LNCaP cells were treated with 100 nM of the bispecific antisense (its approximate IC50 in PC-3 and LNCaP cells), plus various concentrations of anti-clusterin antisense or control ODN, and clusterin levels were analyzed by Western blotting. In both cell lines, bispecific-antisense-induced up-regulation of clusterin was significantly inhibited by the anti-clusterin antisense.

Example 7

Figure 6A:
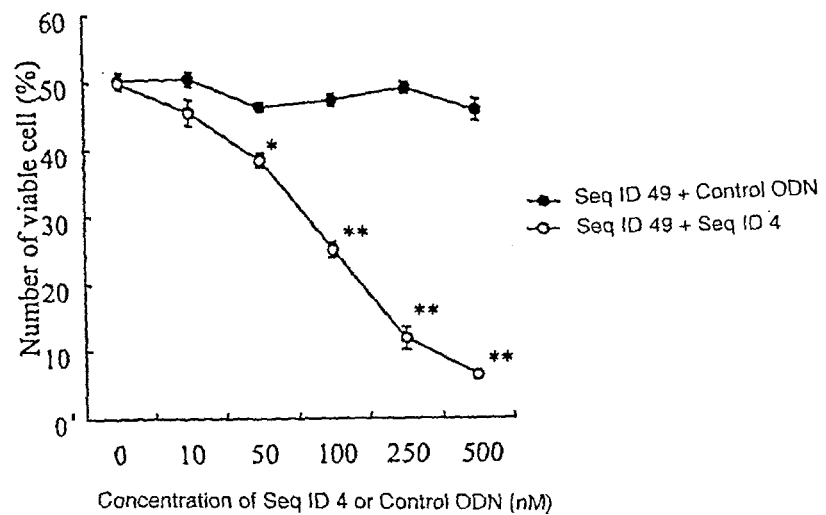
FIGS. 6A-D show results for combination therapy using a bispecific antisense targeting both IGFBP-2 and IGFBP-5 and anti-clusterin antisense.
Figure 6B:
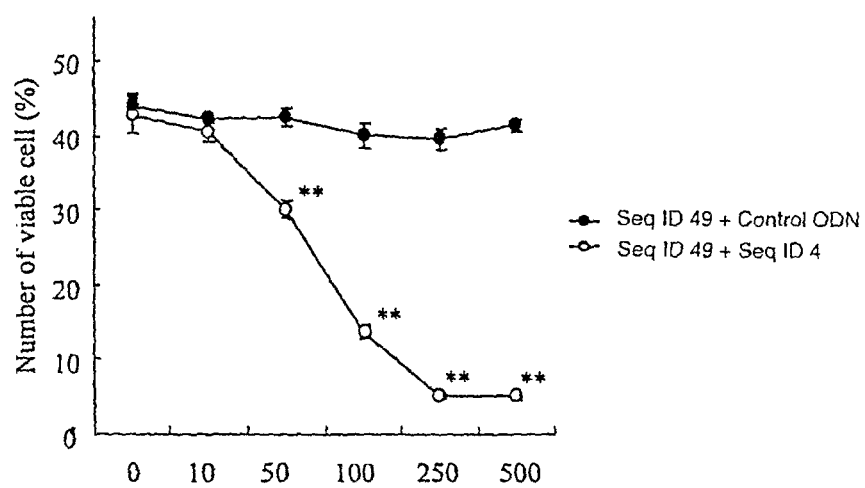
Figure 6C:
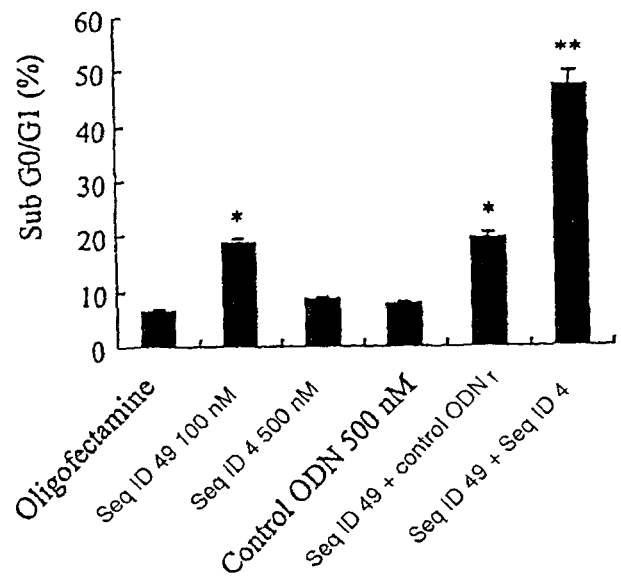
Figure 6D:
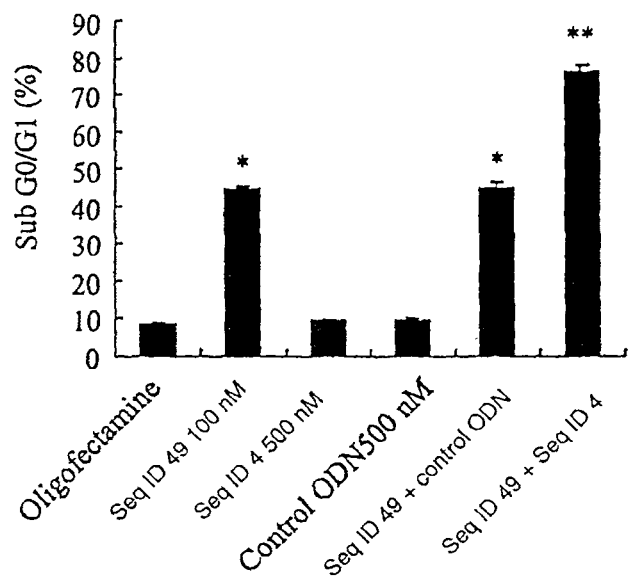

We next tested whether anti-clusterin antisense knockdown of bispecific antisense-induced increases in clusterin enhanced apoptotic rates. PC-3 and LNCaP cells were treated daily with 100 nM of the bispecific antisense and various concentrations of anti-clusterin antisense or control ODN for 2 days. After 72 hours incubation, cell viability was determined by the MTT or crystal violet assay, respectively. As shown in FIGS. 6, A and B, the combination with the anti-clusterin antisense significantly enhanced the cytotoxicity of the bispecific antisense in a dose-dependent manner in both PC-3 and LNCaP cells. In contrast, the anti-clusterin antisense had no effects on apoptotic rates when used alone. Combined treatment of bispecific antisense plus anti-clusterin antisense significantly increased the sub G0/G1 fraction compared to controls in both PC-3 and LNCaP cells (FIGS. 6C and D). We further evaluated the effects of combined treatment on apoptosis using Western blot analysis to identify PARP cleavage, a substrate for caspases activated during apoptotic execution (Labnik et al. *Nature* 371: 346-347 (1994). In PC-3 cells the 85 kD PARP cleaved fragment was detected only after combined treatment with >100 nM of anti-clusterin antisense treatment. Similarly, increased levels of cleaved PARP was detected in LNCaP cells after treatment with bispecific antisense plus >100 nM anti-clusterin antisense.

Example 8

Figure 7A:
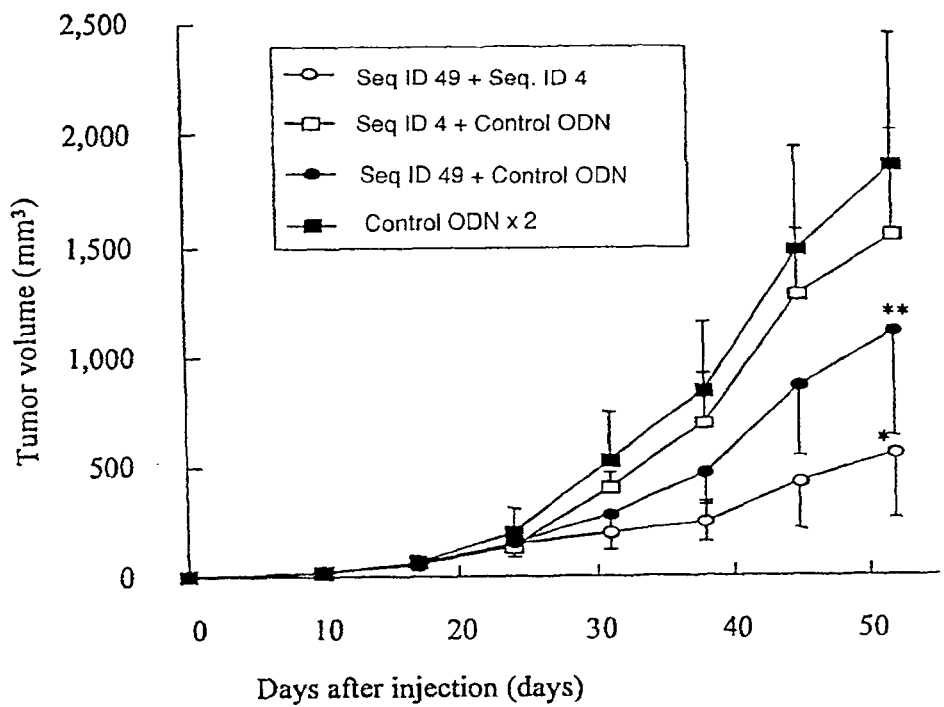
FIGS. 7A-C shows results for treatment of PC-3 cells with combination therapy using a bispecific antisense targeting both IGFBP-2 and IGFBP-5 and anti-clusterin antisense.
Figure 7B:
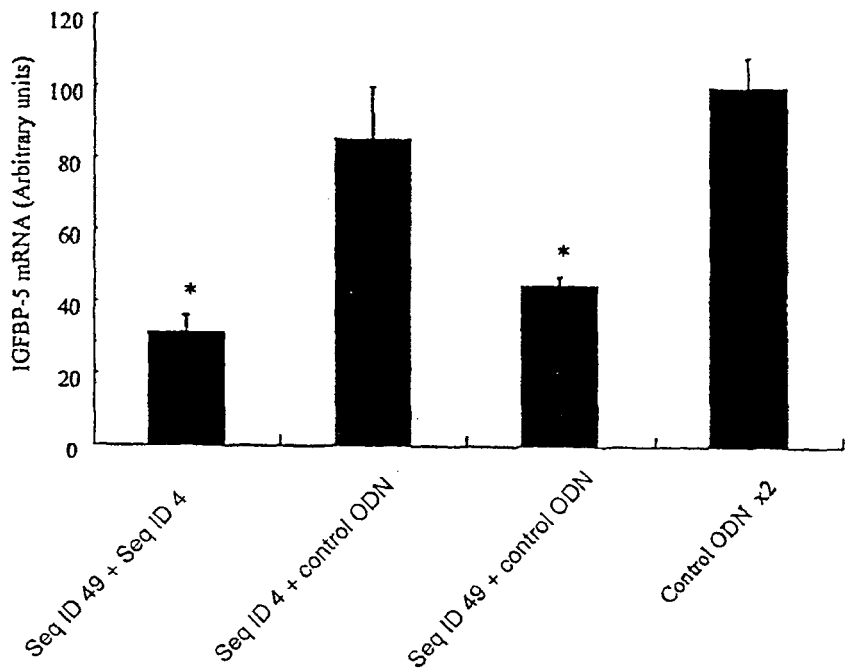
Figure 7C:
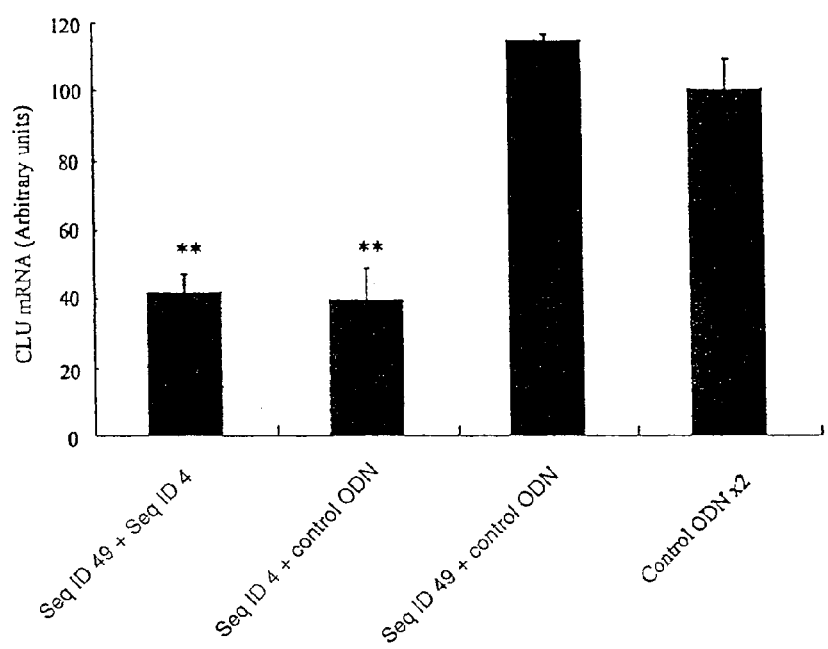
Figure 8A:
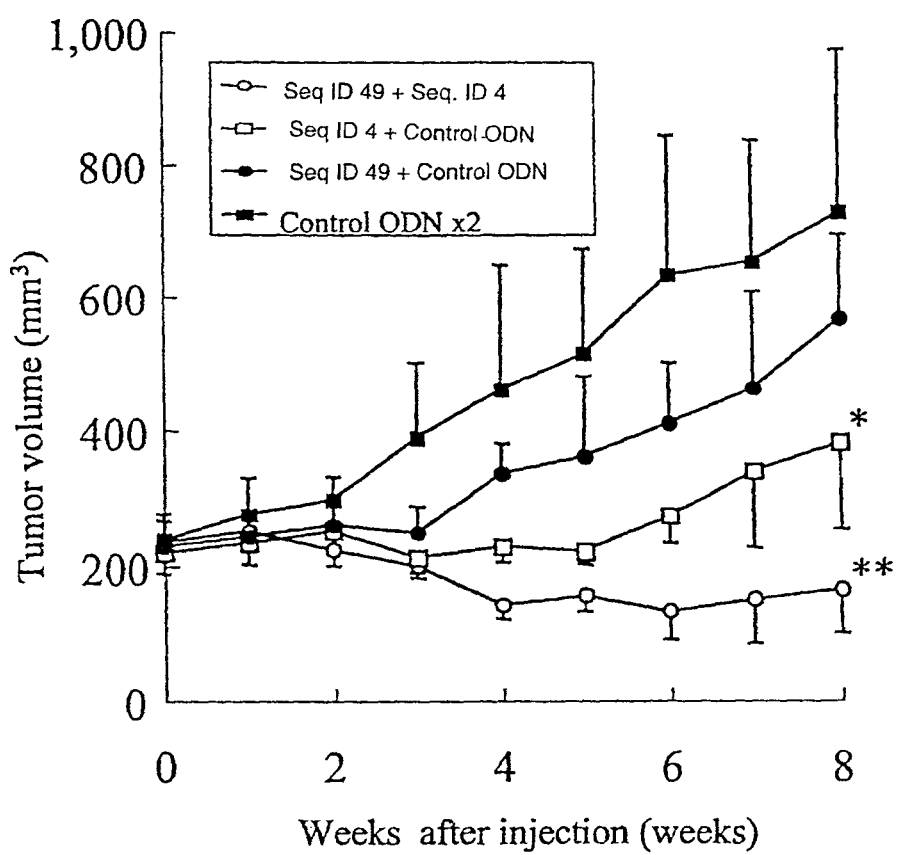
FIGS. 8A-E shows results for treatment of PC-3 cells with combination therapy using a bispecific antisense targeting both IGFBP-2 and IGFBP-5 and anti-clusterin antisense.
Figure 8B:
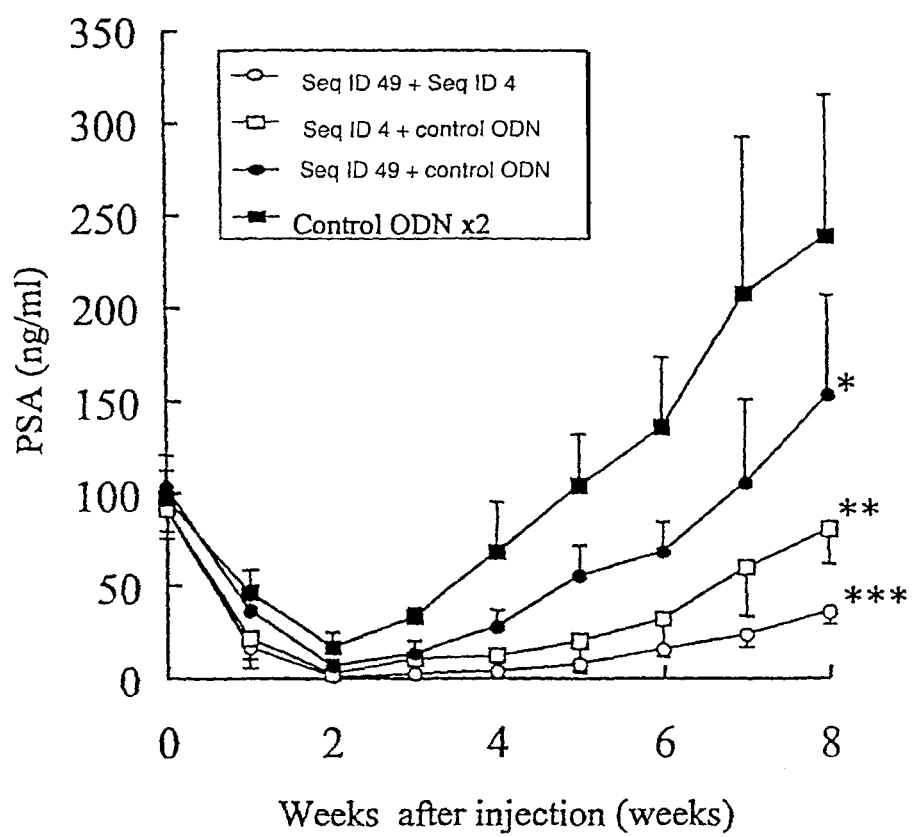
Figure 8C:
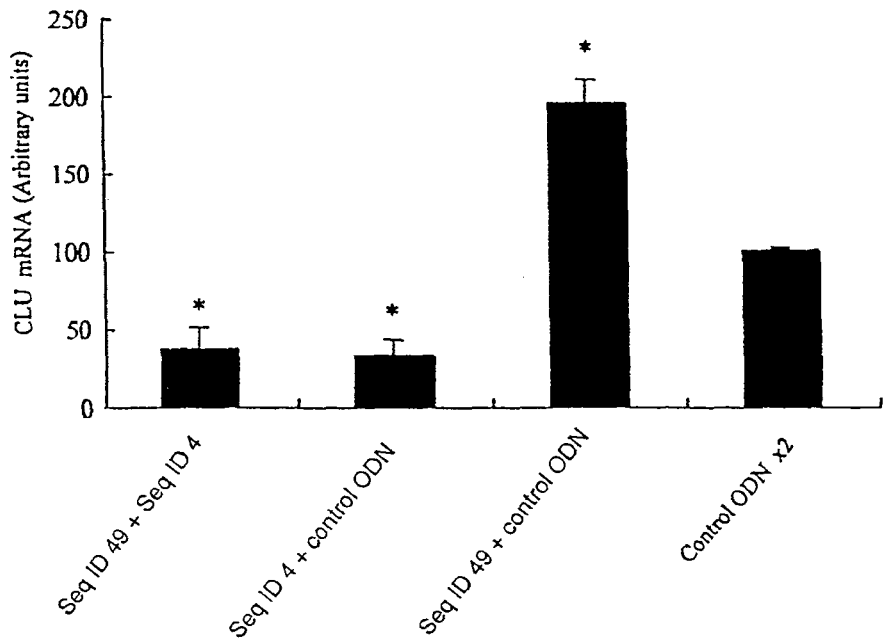
Figure 8D:
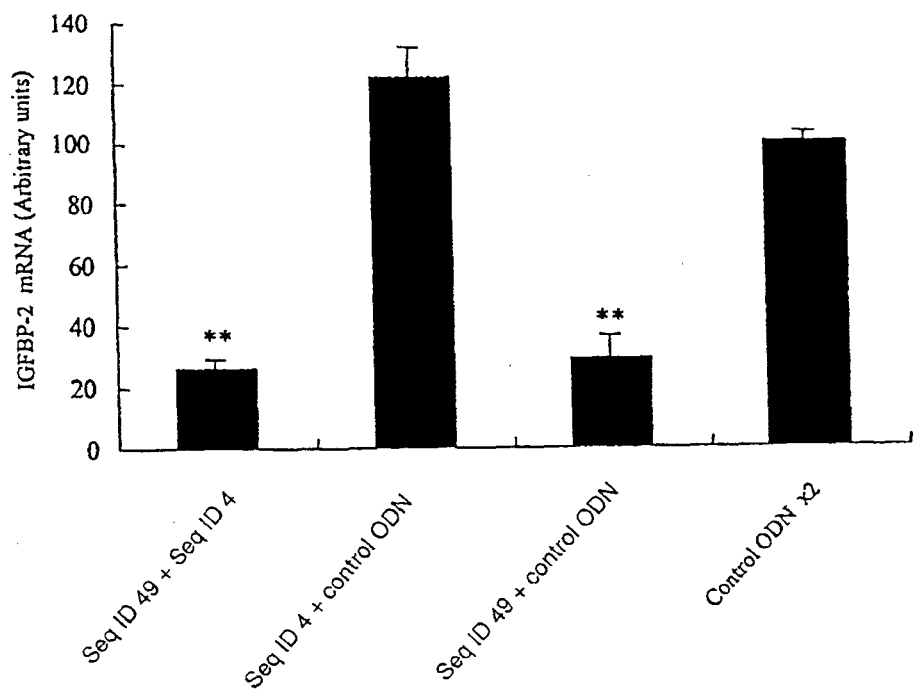
Figure 8E:
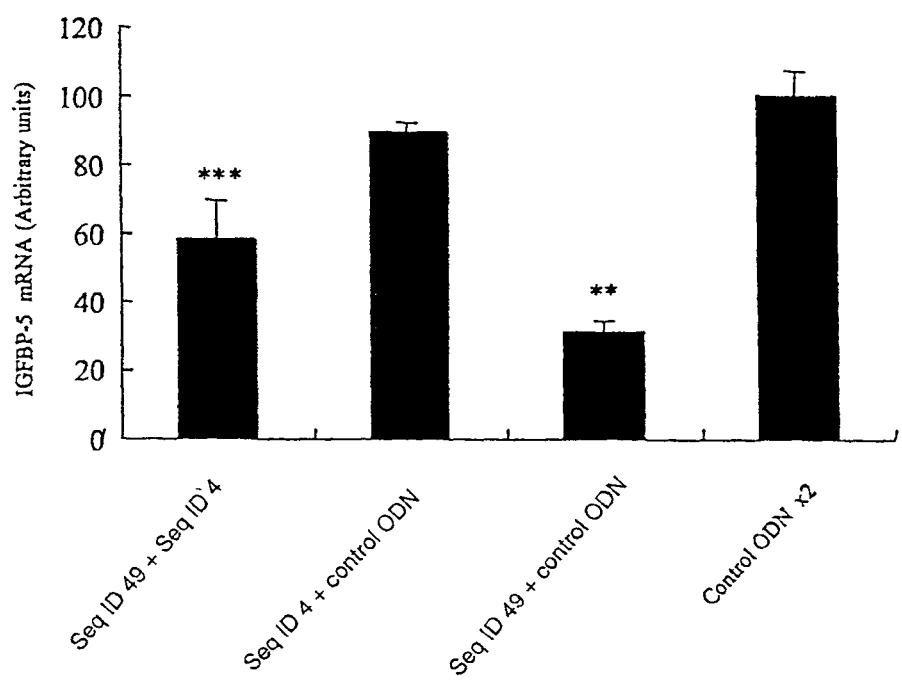

We next tested whether the in vitro observations above could be recapitulated in vivo. Male mice bearing PC-3 tumors (100 mm$^3$) were randomly selected for treatment with bispecific antisense plus anti-clusterin antisense, anti-clusterin antisense plus control ODN, bispecific antisense plus control ODN or control ODN alone. Each treatment group consisted of 10 mice and each mouse received 12.5 mg/kg of bispecific antisense, anti-clusterin antisense and/or control ODN administrated once daily by i.p. during the first week and 3 times per week thereafter. Treatments were continued for 5 weeks after starting ASO injection. Under this experimental condition, no adverse effects were observed. As shown in FIG. 7A, bispecific antisense plus control ODN treatment reduced PC-3 tumor volume by 41% compared to control ODN alone (p<0.05), whereas no significant difference was observed between anti-clusterin antisense plus control ODN or control ODN alone treatment groups. Combined treatment of bispecific antisense plus anti-clusterin antisense significantly inhibited PC-3 tumor growth by 52, 64 and 71% compared to bispecific antisense, anti-clusterin antisense and control ODN treatment groups, respectively. Total RNA was extracted from each tumor after sacrifice and assessed for changes in mRNA levels of IGFBP-5 and clusterin using Northern blot analysis. As shown in FIGS. 7B and C, mRNA levels of IGFBP-5 in PC-3 tumors were significantly reduced by bispecific antisense containing treatment regimen when compared to other treatment regimens. Similarly, mRNA levels of clusterin in PC-3 tumors were significantly reduced by anti-clusterin antisense containing regimen compared to other treatment regimens. Clusterin mRNA level was increased after treatment with bispecific antisense plus control ODN by 15% compared to control ODN alone. Mice bearing subcutaneous LNCaP tumors were castrated and treated with the same schedule described above for PC-3 tumors. Each treatment group consisted of 10 mice. As shown in FIG. 8A, anti-clusterin antisense plus control ODN treatment significantly reduced LNCaP tumor volume by 47% compared to control ODN alone (p<0.01). Although bispecific antisense plus control ODN treatments reduced LNCaP tumor volume by 22% compared to control ODN alone, the difference did not reached statistical significance. Combined treatment with bispecific antisense and anti-clusterin antisense significantly inhibited LNCaP tumor growth by 61, 57 and 77% compared to bispecific antisense, anti-clusterin antisense and control ODN treatment groups, respectively. Serum PSA decreased by approximately 80% by 2 weeks in all treatment groups after castration, and then increased in the control ODN and bispecific antisense plus control ODN groups by 2.5- and 1.5-fold, respectively by 8 weeks post castration. Serum PSA in anti-clusterin antisense plus control ODN and anti-clusterin antisense plus bispecific antisense treatment group remained below baseline levels for longer than 8 weeks post treatment (FIG. 8B). Total RNA was extracted from each tumor after sacrifice and assessed for changes in mRNA levels of clusterin, IGFBP-2 and IGFBP-5 using Northern blot analysis. As shown in FIGS. 8, C, D, and E, mRNA levels of clusterin in LNCaP tumors were significantly reduced by anti-clusterin antisense containing regimen compared to other treatment regimens. Similarly, mRNA levels of IGFBP-2 and IGFBP-5 in LNCaP tumors were significantly decreased by bispecific antisense containing treatment regimen when compared to other treatment regimens. Clusterin mRNA level was significantly increased after treatment with bispecific antisense plus control ODN by 2-fold compared to control ODN alone. These data, observed both in PC-3 and LNCaP tumor model, mirror the in vitro observations above, with bispecific antisense-induced up-regulation of clusterin and anti-clusterin antisense mediated suppression of bispecific antisense-induced clusterin up-regulation.

All of the cited documents are incorporated herein by reference in those jurisdictions allowing such incorporation.

While specific embodiments of the invention have been described and illustrated, such embodiments should be considered illustrative of the invention only and not as limiting the invention.

REFERENCES

1. Wong et al., *Eur. J. Biochem.* 221 (3), 917-925 (1994)
2. Sensibar et al., *Cancer Research* 55: 2431-2437 (1995)
3. Fire et al. (1998) *Nature* 391, 806-811
4. Carthew et al. (2001) Current Opinions in Cell Biology 13, 244-248.

The invention claimed is:

1. A therapeutic combination for treatment of cancer comprising
   (a) means for reducing IGFBP-2 and/or IGFBP-5 in cancer cells; and
   (b) means for reducing the effective amount of clusterin in cancer cells.

* * * * *

UNITED STATES PATENT AND TRADEMARK OFFICE
CERTIFICATE OF CORRECTION

PATENT NO. : 8,541,390 B2  
APPLICATION NO. : 13/469402  
DATED : September 24, 2013  
INVENTOR(S) : Martin Gleave Page 1 of 2

It is certified that error appears in the above-identified patent and that said Letters Patent is hereby corrected as shown below:

In the Specification

In Columns 7 and 8, TABLE 1 should read:

| Seq ID No. | Description | SEQUENCE (5' to 3') |
|---|---|---|
| 2 | Antisense TRPM-2 oligonucleotide | GCACAGCAGGAGAATCTTCAT |
| 3 | Antisense TRPM-2 oligonucleotide | TGGAGTCTTTGCACGCCTCGG |
| 4 | Antisense oligonucleotide corresponding to the humanTRPM-2 translation initiation site | CAGCAGCAGAGTCTTCATCAT |
| 5 | Antisense TRPM-2 oligonucleotide | ATTGTCTGAGACCGTCTGGTC |
| 6 | Antisense TRPM-2 oligonucleotide | CCTTCAGCTTTGTCTCTGATT |
| 7 | Antisense TRPM-2 oligonucleotide | AGCAGGGAGTCGATGCGGTCA |
| 8 | Antisense TRPM-2 oligonucleotide | ATCAAGCTGCGGACGATGCGG |
| 9 | Antisense TRPM-2 oligonucleotide | GCAGGCAGCCCGTGGAGTTGT |
| 10 | Antisense TRPM-2 oligonucleotide | TTCAGCTGCTCCAGCAAGGAG |
| 11 | Antisense TRPM-2 oligonucleotide | AATTTAGGGTTCTTCCTGGAG |
| 12 | Antisense TRPM-2 oligonucleotide | GCTGGGCGGAGTTGGGGGCCT |
| 20 | 2 base TRPM-2 mismatch oligonucleotide used as a control | CAGCAGCAGAGTATTTATCAT |

Signed and Sealed this  
Twenty-sixth Day of May, 2015

Michelle K. Lee  
*Director of the United States Patent and Trademark Office*

In Column 7, lines 19-21 should read: -- consisting of Seq. ID. Nos.: 2 to 12 as shown in Table 1, or more specifically Seq. ID. No. 4, Seq. ID. No. 5 and Seq. ID. No. 12. --